(12) United States Patent
Peine et al.

(10) Patent No.: US 10,874,470 B2
(45) Date of Patent: Dec. 29, 2020

(54) PASSIVE AXIS SYSTEM FOR ROBOTIC SURGICAL SYSTEMS

(71) Applicant: Covidien LP, Mansfield, MA (US)

(72) Inventors: William Peine, Ashland, MA (US); Cameron Cecil, Boston, MA (US)

(73) Assignee: Covidien LP, Mansfield, MA (US)

( * ) Notice: Subject to any disclaimer, the term of this patent is extended or adjusted under 35 U.S.C. 154(b) by 63 days.

(21) Appl. No.: 16/306,801

(22) PCT Filed: May 25, 2017

(86) PCT No.: PCT/US2017/034433
§ 371 (c)(1),
(2) Date: Dec. 3, 2018

(87) PCT Pub. No.: WO2017/210074
PCT Pub. Date: Dec. 7, 2017

(65) Prior Publication Data
US 2019/0183595 A1    Jun. 20, 2019

Related U.S. Application Data

(60) Provisional application No. 62/345,090, filed on Jun. 3, 2016.

(51) Int. Cl.
*A61B 34/00* (2016.01)
*A61B 34/37* (2016.01)

(52) U.S. Cl.
CPC .............. *A61B 34/74* (2016.02); *A61B 34/25* (2016.02); *A61B 34/37* (2016.02); *A61B 34/71* (2016.02)

(58) Field of Classification Search
CPC ......... A61B 34/74; A61B 34/71; A61B 34/31; A61B 34/25
See application file for complete search history.

(56) References Cited

U.S. PATENT DOCUMENTS 7,391,177 B2   6/2008   Kishi et al.
8,828,023 B2   9/2014   Neff et al.
(Continued)

FOREIGN PATENT DOCUMENTS

DE   2600957 A1   7/1976
FR   2950830 A1   4/2011

OTHER PUBLICATIONS

International Search Report and Written Opinion corresponding to counterpart Int'l Appln. No. PCT/US17/034433 dated Sep. 4, 2017.
(Continued)

*Primary Examiner* — Kawing Chan
*Assistant Examiner* — Bradley R Brown
(74) *Attorney, Agent, or Firm* — Carter, DeLuca & Farrell LLP

(57) ABSTRACT

A robotic surgical system has a user interface with a control arm that includes a passive axis system for maintaining degrees-of-freedom of a gimbal rotatably supported on the control arm as the gimbal is manipulated during a surgical procedure. The control arm includes a swivel member, a first member, and a second member. The swivel member is rotatable about a first axis. The first member rotatably coupled to the swivel member about a second axis that is orthogonal to the first axis. The second member rotatably coupled to the first member about a third axis that is parallel to the second axis. The gimbal rotatably supported by the second member about a fourth axis that is orthogonal to the third axis. The passive axis system correlating rotation of the swivel member about the first axis with rotation of the gimbal about the fourth axis.

13 Claims, 22 Drawing Sheets

(56) References Cited

U.S. PATENT DOCUMENTS

| | | |
|---|---|---|
| 9,241,768 B2 | 1/2016 | Sandhu et al. |
| 2003/0023346 A1* | 1/2003 | Salisbury, Jr. ......... A61B 34/70 |
| | | 700/245 |
| 2004/0186345 A1 | 9/2004 | Yang et al. |
| 2005/0222830 A1* | 10/2005 | Massie .................... G06F 3/014 |
| | | 703/6 |
| 2015/0045812 A1* | 2/2015 | Seo ........................ A61B 34/30 |
| | | 606/130 |
| 2015/0090065 A1 | 4/2015 | Kishi |
| 2016/0334638 A1* | 11/2016 | Wagner ................ G03B 17/561 |
| 2017/0159875 A1* | 6/2017 | Wagner ................ F16M 11/105 |

OTHER PUBLICATIONS

Extended European Search Report dated Jan. 7, 2020 corresponding to counterpart Patent Application EP 17807266.6.
Extended European Search Report dated Jan. 7, 2020 corresponding to counterpart Patent Application EP 17807265.8.

* cited by examiner

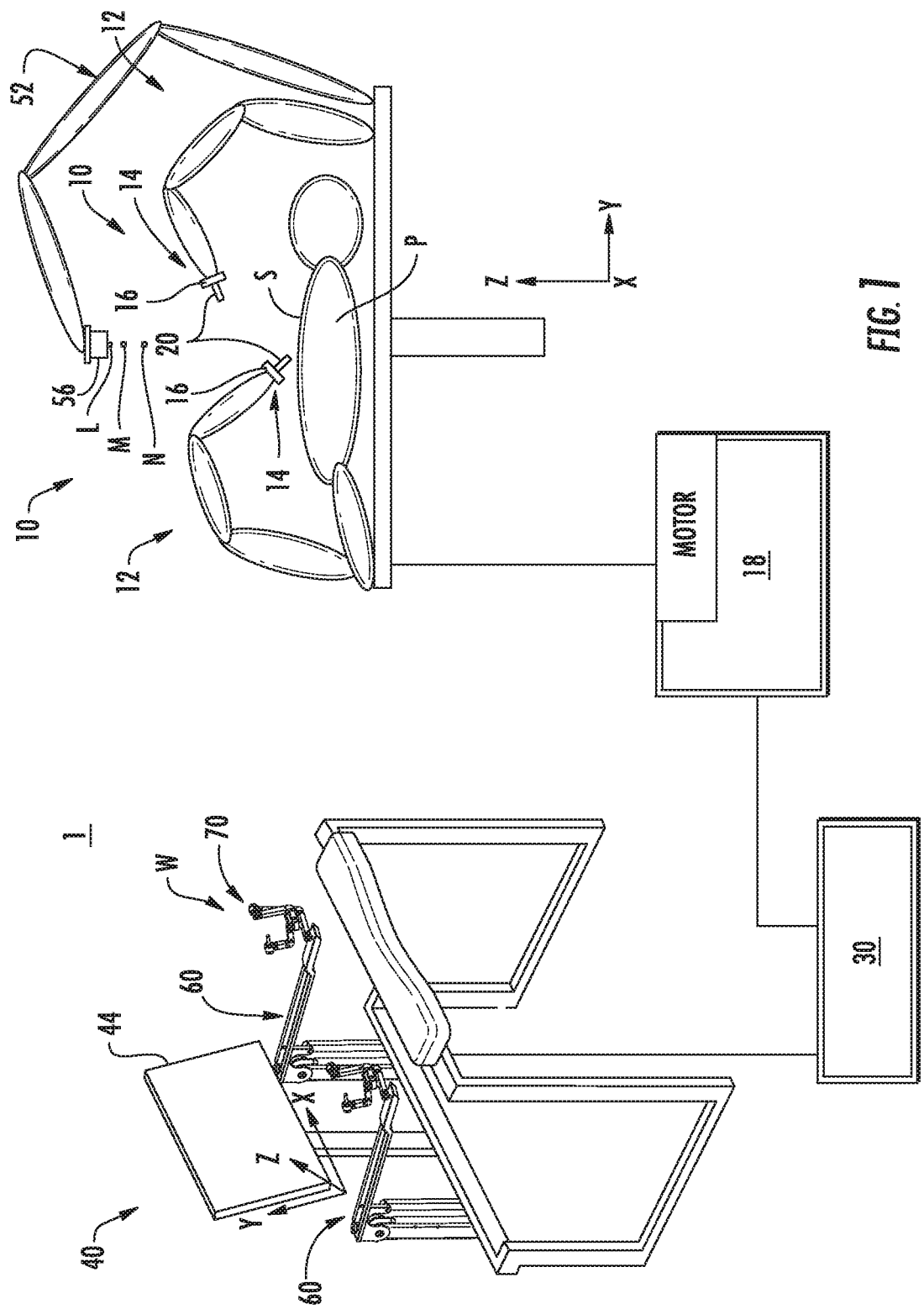

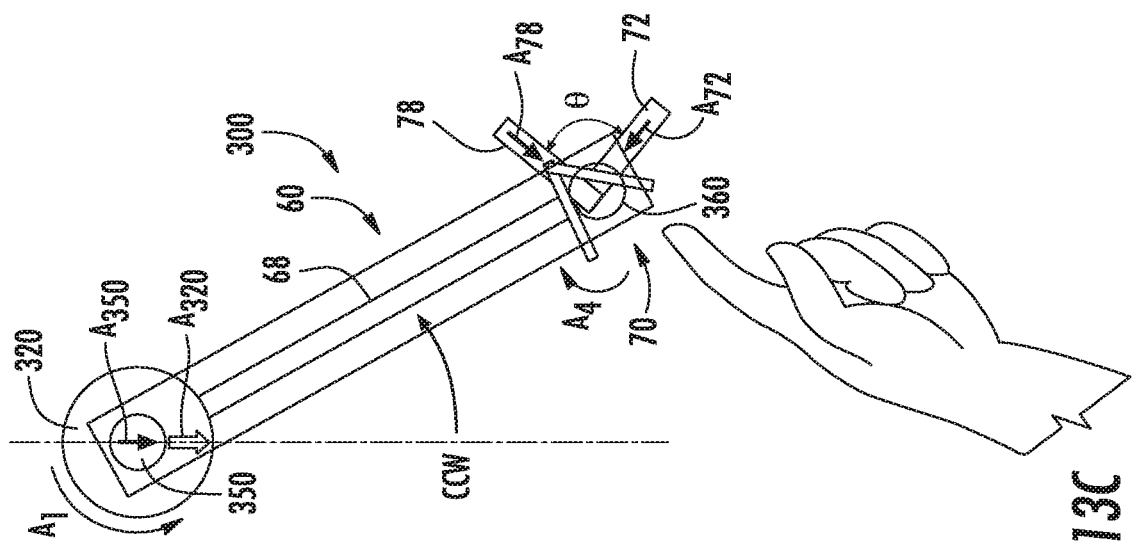
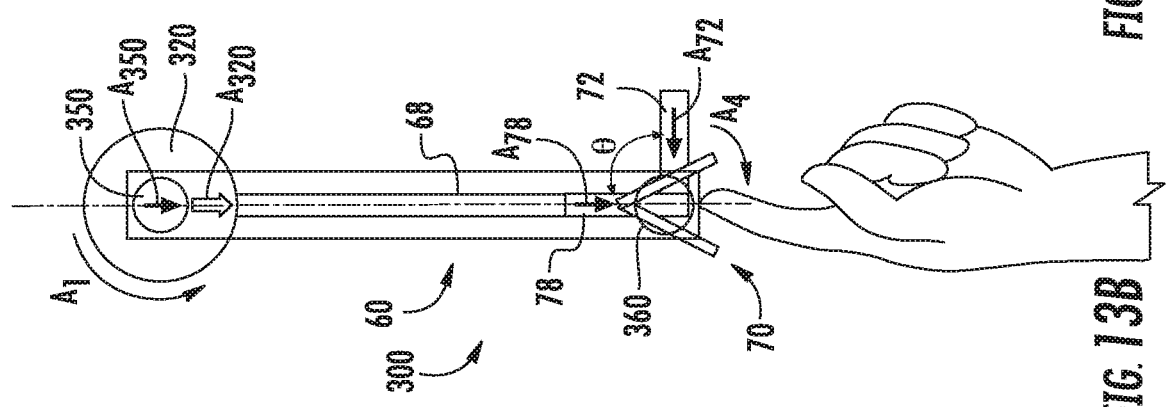
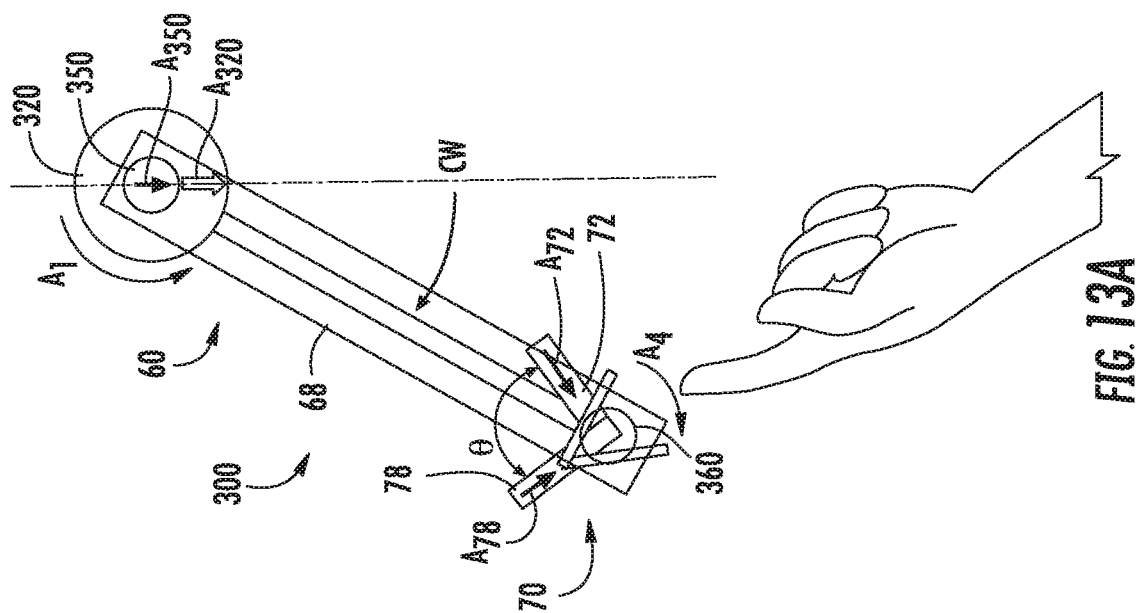

PASSIVE AXIS SYSTEM FOR ROBOTIC SURGICAL SYSTEMS

CROSS-REFERENCE TO RELATED APPLICATIONS

This application is a U.S. National Stage Application filed under 35 U.S.C. § 371(a) of International Patent Application Serial No. PCT/US2017/034433, filed May 25, 2017, which claims the benefit of and priority to U.S. Provisional Patent Application Ser. No. 62/345,090, filed Jun. 3, 2016, the entire disclosure of which is incorporated by reference herein.

BACKGROUND

Robotic surgical systems have been used in minimally invasive medical procedures. During a medical procedure, the robotic surgical system is controlled by a surgeon interfacing with a user interface. The user interface allows the surgeon to manipulate an end effector that acts on a patient. The user interface includes an input controller that is moveable by the surgeon to control the robotic surgical system.

The input controller of the user interface includes a gimbal that is engaged by a surgeon to allow the surgeon to manipulate the end effector. Gimbals typically include multiple linkages that are moveable relative to one another. As the input control is engaged by the surgeon, the linkages of the gimbal can become splayed, encounter singular conditions, or reach limit stops of the gimbal joints, which reduce the degrees-of-freedom of the gimbal.

Reduction in the degrees-of-freedom of the gimbal may reduce the ability of the surgeon to manipulate the end effector as needed during a surgical procedure.

SUMMARY

This disclosure relates generally to a passive axis system for maintaining the degrees-of-freedom of a gimbal as the gimbal is engaged or manipulated during a surgical procedure. The passive axis system induces an opposite relative motion of a joint located at the base of the gimbal to the rotation of a control arm to prevent linkages of the gimbal from splaying, encountering singular conditions, or nesting relative to one another.

In an aspect of the present disclosure, a control arm for receiving input from a user includes a swivel member, a first member, a second member, a gimbal, and a passive axis system. The swivel member is rotatable about a first axis. The first member has upper and lower ends. The lower end is rotatably coupled to the swivel member about a second axis that is orthogonal to the first axis. The second member has first and second ends. The first end is pivotally coupled to the upper end of the first member about a third axis that is parallel to the second axis. The gimbal is rotatably coupled to the second end of the second member about a fourth axis that is orthogonal to the third axis. The passive axis system is configured to rotatably associate rotation of the first member about the first axis with rotation of the gimbal about the fourth axis. The passive axis system includes the lower disk, a first shaft, an upper disk, a wire loop, and a second shaft. The lower disk is rotatably positioned about the first axis adjacent to the lower end of the first member. The upper disk is positioned adjacent the first end of the second member. The first shaft is disposed within the first member and is configured to rotatably couple the lower disk to the upper disk. The wire loop rotatably couples the upper disk to the second shaft.

In aspects, the lower disk is rotatably fixed relative to the swivel member. The passive axis system may include a lower universal joint that is positioned such that the lower universal joint pivots about the second axis as the first member rotates about the second axis. The lower universal joint may be rotatably coupled to the lower end of the first shaft and the lower disk. The passive axis system may include an upper universal joint that is positioned such that the upper universal joint pivots about the third axis as the second member rotates about the third axis.

In some aspects, the second shaft rotates the gimbal about the fourth axis in response to rotation of the swivel member about the first axis. The second shaft may rotate the gimbal in a second direction in response to rotation of the swivel member in a first direction that is opposite to the second direction. Rotation of the second shaft in the second direction is angularly scaled and opposite to rotation of the swivel member in the first direction.

In particular aspects, the control arm includes a fixed mount and the swivel member is rotatably coupled to the fixed mount about the first axis. The first disk may be rotatably fixed relative to the fixed mount.

In certain aspects, the control arm includes a gimbal disk that is disposed within the second end of the second member that is rotatable about the fourth axis. The wire loop may pass around the upper disk and the gimbal disk.

In aspects, the control arm includes a gimbal shaft that is positioned along and rotatably about the fourth axis. The gimbal shaft may be rotatably coupled to the gimbal disk. The gimbal may include a support arm, a swing arm, an input support arm, and an input shaft. The support arm may have a first end that is rotatably fixed to the gimbal shaft. The swing arm may have a first end that is rotatably coupled about a fifth axis to a second end of the support arm. The input support arm may have a first end that is rotatably coupled about a sixth axis to a second end of the swing arm. The input shaft may be positioned along a seventh axis and rotatably coupled to a second of the input support arm.

In another aspect of the present disclosure, a control arm for receiving input from a user includes a swivel member, a first member, a second member, a gimbal, and a passive axis system. The swivel member is rotatable about a base axis. The first member extends from the swivel member to an upper end. The second member has a first end that is coupled to the upper end of the first member. The gimbal is rotatably coupled about a gimbal axis to a second end of the second member. The passive axis system is configured to rotatably associate rotation of the first member about the base axis with rotation of the gimbal about the gimbal axis to maintain an angle of the gimbal relative to the swivel member.

In another aspect of the present disclosure, a robotic surgical system includes a processing unit, a robotic system, and a user interface. The robotic system is in communication with the processing unit and includes a first tool supported at an end of a first link. The user interface is in communication with the processing unit and includes a first control arm. The first control arm is configured to manipulate the first link and the first tool of the robotic system in response to input from a user. The first control arm may be any of the control arms detailed herein.

In aspects, the robotic system includes a second tool supported at an end of a second link and the user interface includes a second control arm. The second control arm may be configured to manipulate the second link and the second tool in response to input from a user. The second control arm may be any of the control arms detailed herein.

In another aspect of the present disclosure, a method of control a tool of a robotic system with a user interface includes moving a gimbal of the user interface such that a control arm, supporting the gimbal, is rotated about a first axis. The control arm may include a passive axis system that rotates a support arm of the gimbal about a second axis to maintain an angle between the support arm of the gimbal and an input shaft of the gimbal. The control arm may be any of the control arms disclosed herein.

In another aspect of the present disclosure, a control arm for receiving input from a user includes a swivel member a first member, a second member, a gimbal, and a limit extending mechanism. The swivel member is rotatable about a first axis in a first base direction to a first rotational limit and in a second base direction opposite the first direction to a second rotational limit. The first member is pivotally coupled to the swivel member. The second member is pivotally coupled to the first member. The gimbal is rotatably supported about a fourth axis by the second member. Rotation of the gimbal about the fourth axis is operably associated with rotation of the swivel member about the first axis such that rotation of the gimbal in a first gimbal direction rotates the swivel member relative to the base about the first axis in the first base direction. The limit extending mechanism is configured to allow the gimbal to rotate about the fourth axis in the first gimbal direction when the swivel member is at the first rotational limit when an input torque in the first gimbal direction exceeds a threshold torque of the limit extending mechanism about the first axis. The threshold torque may be in a range of about 200 Nmm to about 1200 Nmm.

In aspects, the rotation of the gimbal in a second direction opposite the first direction rotates the swivel member relative to the base about the first axis in the second base direction.

In some aspects, the limit extending mechanism includes a plunger that supports a cam follower and a cam. The cam may have a camming surface and the plunger may bias the cam follower into engagement with the camming surface of the cam. The camming surface of the cam may include a well. The cam may have a centered position when the cam follower is positioned within the well of the cam. The cam may be biased to the centered position by the engagement of the cam follower with the camming surface of the cam. The threshold force may be equal to a torque required to rotate the cam from the centered position. The camming surface may define a cam profile from the well to a midpoint of the camming surface. The cam profile may be shaped such that a constant input torque equal to the threshold force is required for continued rotation of the cam to traverse the camming surface with the cam follower from the well towards the midpoint. Alternatively, the cam profile may be shaped such that an increasing input torque is required for continued rotation of the cam to traverse the camming surface with the cam follower from the well towards the midpoint. The radius of the cam profile may increase such that a linearly increasing input torque is required for continued rotation of the cam or the radius of the cam provide may increase such that an exponentially increasing input torque is required for continued rotation of the cam.

In certain aspects, the limit extending mechanism includes a drive shaft, a first pulley, a second pulley, and a drive belt. The first pulley may be rotatably fixed to the drive shaft of the motor. The second pulley may be rotatably fixed about the first axis and may be operably associated with the fourth axis. The drive belt may be disposed about the first and second pulleys. The motor may prevent rotation of the drive shaft when the input force is less than the threshold force.

In another aspect of the present disclosure, a method of controlling a tool of a robotic system with a user interface includes moving a gimbal of the user interface and applying an input force to the gimbal. Moving the gimbal of the user interface rotates a control arm that supports the gimbal about a first axis in a first direction until the gimbal reaches a threshold limit. The control arm includes a limit exceeding mechanism that resists rotation of the gimbal in the first direction beyond the threshold limit. Appling the input torque to the gimbal in the first direction includes applying an input torque greater than a threshold force of the limit exceeding mechanism such that the gimbal is rotated beyond the threshold limit.

In aspects, the method includes releasing the gimbal after the gimbal is rotated beyond the threshold limit such that the limit exceeding mechanism returns the gimbal to the threshold limit. The control arm may be rotatably fixed about the first axis as the gimbal is rotated beyond the threshold limit.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein:

FIG. 1 is a schematic illustration of a user interface and a robotic system in accordance with the present disclosure;

FIGS. 13A-C are schematic illustrations of the passive axis system correlating rotation of the control arm about a first axis of rotation with rotation of a support arm of the gimbal about a fourth axis of rotation;

DETAILED DESCRIPTION

Figure 2C:
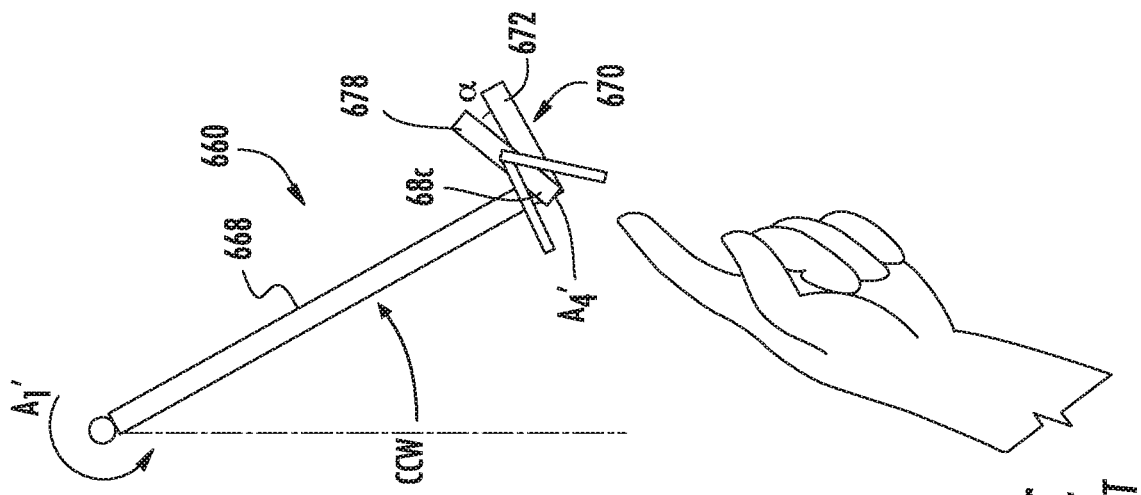
FIG. 2A-C are schematic illustrations of a prior art control arm and gimbal in response to rotation about a first axis of rotation.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is farthest from the clinician.

A passive axis system in accordance with the present disclosure is configured to rotate a gimbal supported by a control arm of a user interface as the control arm is rotated about its base. The passive axis system rotates the gimbal in an opposite direct to the rotation of the control arm to prevent the gimbal from reducing its degrees-of-freedom of movement by linkages of the gimbal splaying or nesting with one another. The passive axis system may include a first or lower pulley that is positioned at the base to rotate the gimbal relative to the base as the control arm is rotated. The lower pulley is operatively coupled to a gimbal pulley that is disposed at the end of a horizontal member of the control arm such that the gimbal pulley is rotated in an opposite direction to rotation of the control arm about the base to rotate a support link of the gimbal. The gimbal pulley may be rotatably fixed at one end of a gimbal shaft which is rotatably fixed at its other end to a first end of the support arm of the gimbal.

By maintaining the degrees-of-freedom, the gimbal links may also be maintained near an optimal angle relative to one another (e.g., 90°). This may maintain symmetrical inertia in all rotation axes of links of the gimbal (i.e., roll, pitch, and yaw). By preventing the gimbal from splaying or nesting, the rotational coupling between the joints is minimized such that the inertia will feel the same to the user in all rotation directions which prevents the gimbal from feeling heavy one rotation direction compared to another.

Referring to FIG. 1, a robotic surgical system 1 is shown generally as a robotic system 10, a processing unit 30, and a user interface 40. The robotic system 10 generally includes linkages 12 and a robot base 18. The linkages 12 moveably support an end effector or tool 20 which is configured to act on tissue. The linkages 12 may be in the form of arms or links each having an end 14 that supports an end effector or tool 20 which is configured to act on tissue. In addition, the ends 14 of the linkages 12 may include an imaging device 16 for imaging a surgical site "S". The user interface 40 is in communication with robot base 18 through the processing unit 30.

The user interface 40 includes a display device 44 which is configured to display three-dimensional images. The display device 44 displays three-dimensional images of the surgical site "S" which may include data captured by imaging devices 16 positioned on the ends 14 of the linkages 12 and/or include data captured by imaging devices that are positioned about the surgical theater (e.g., an imaging device positioned within the surgical site "S", an imaging device positioned adjacent the patient "P", imaging device 56 positioned at a distal end of an imaging linkage 52). The imaging devices (e.g., imaging devices 16, 56) may capture visual images, infra-red images, ultrasound images, X-ray images, thermal images, and/or any other known real-time images of the surgical site "S". The imaging devices transmit captured imaging data to the processing unit 30 which creates three-dimensional images of the surgical site "S" in real-time from the imaging data and transmits the three-dimensional images to the display device 44 for display.

The user interface 40 also includes input handles attached to gimbals 70 which allow a clinician to manipulate the robotic system 10 (e.g., move the linkages 12, the ends 14 of the linkages 12, and/or the tools 20). Each of the gimbals 70 is in communication with the processing unit 30 to transmit control signals thereto and to receive feedback signals therefrom. Additionally or alternatively, each of the gimbals 70 may include control interfaces or input devices (not shown) which allow the surgeon to manipulate (e.g., clamp, grasp, fire, open, close, rotate, thrust, slice, etc.) the tools 20 supported at the ends 14 of the linkages 12.

Each of the gimbals 70 is moveable to move the ends 14 of the linkages 12 within a surgical site "S". The three-dimensional images on the display device 44 are orientated such that movement of the gimbals 70 moves the ends 14 of the linkages 12 as viewed on the display device 44. It will be appreciated that the orientation of the three-dimensional images on the display device may be mirrored or rotated relative to view from above the patient "P". In addition, it will be appreciated that the size of the three-dimensional images on the display device 44 may be scaled to be larger or smaller than the actual structures of the surgical site "S" permitting the surgeon to have a better view of structures within the surgical site "S". As the gimbal 70 is moved, the tools 20 are moved within the surgical site "S". Movement of the tools 20 may also include movement of the ends 14 of the linkages 12 which support the tools 20.

For a detailed discussion of the construction and operation of a robotic surgical system 1, reference may be made to U.S. Pat. No. 8,828,023, the entire contents of which are incorporated herein by reference.

Figure 2B:
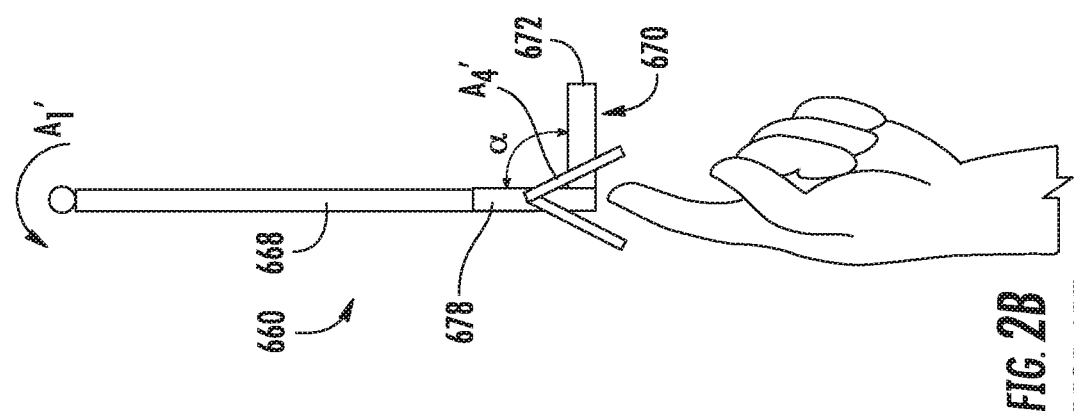
Figure 2A:
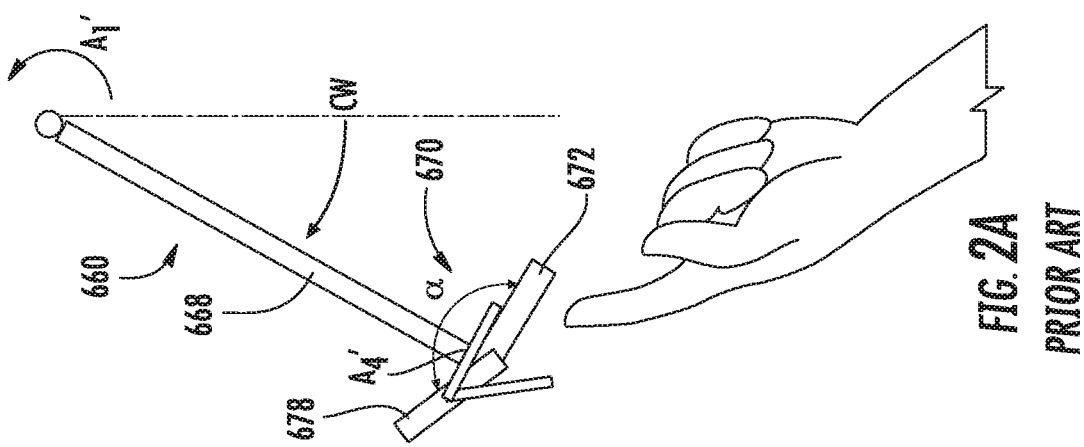

With reference to FIGS. 2A-C, a prior art control arm 660 is represented including an input shaft 678 and a gimbal 670. As the input shaft 678 is engaged to rotate a control arm 660 about the first axis of rotation $A_1'$ from a neutral position (FIG. 2B) to a first position (FIG. 2A) and to a second position (FIG. 2C). As the control arm 660 is rotated without a passive axis system, an angle α defined between a support arm 672 of the gimbal 670 and the input shaft 678 is not maintained. Thus, as the control arm 660 is rotated in a clockwise direction, about the first axis of rotation $A_1'$, the angle α increases such that the support arm 672 and the input support arm 676 are substantially linear or splayed with respect to one another. Similarly, as the control arm 660 is rotated in a counter clockwise direction about the first axis of rotation $A_1'$, the angle α decreases such that the support arm 672 and the input support arm 676 are substantially coincident or nested with one another. As the angle α approaches a linear or coincident value (i.e., 180 or 0 degrees), the degrees-of-freedom of the gimbal 670 will be reduced.

Figure 3:
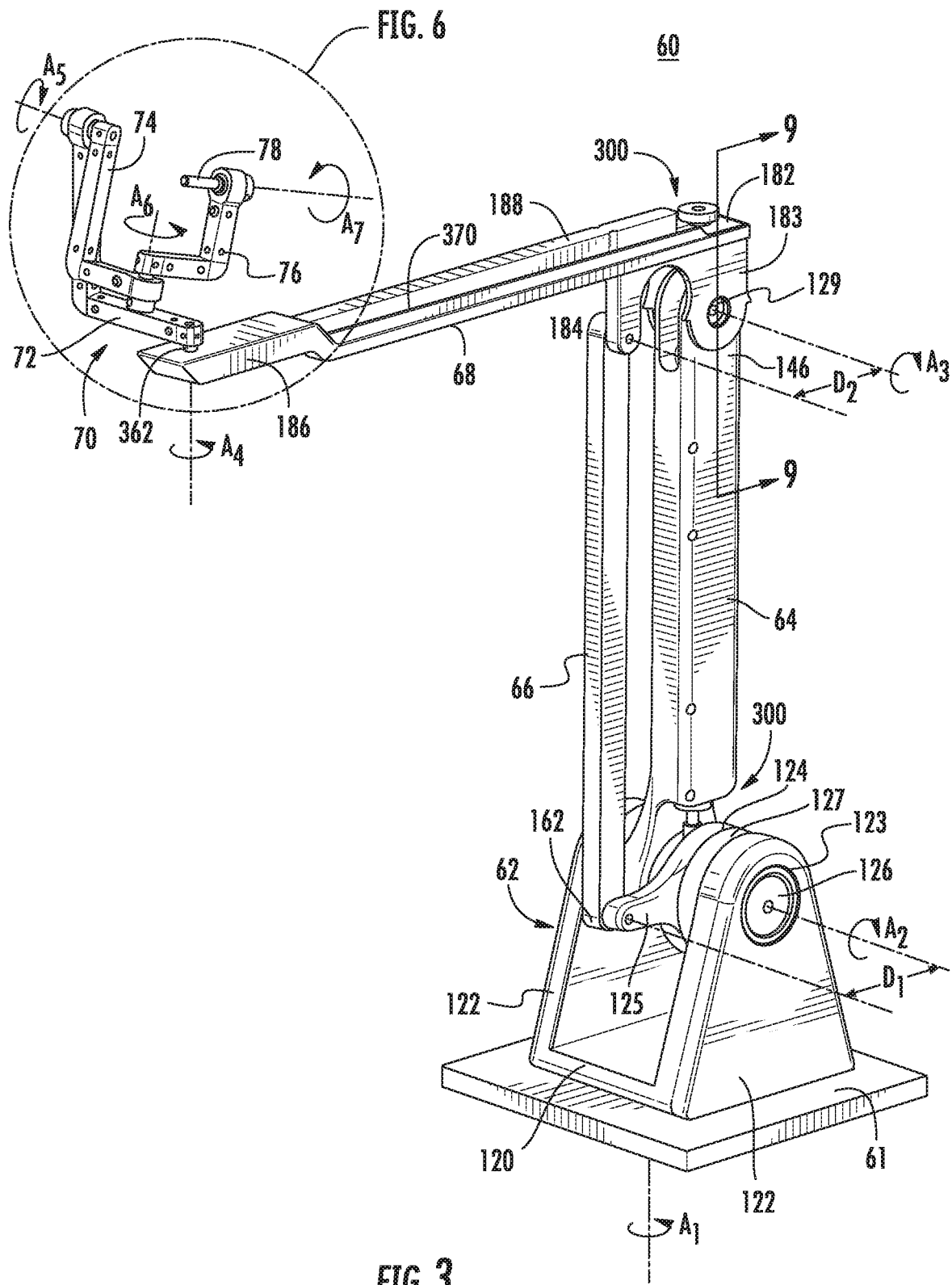
FIG. 3 is a perspective view of a control arm of the user interface of FIG. 1.

Referring to FIG. 3, each control arm 60 of the user interface 40 (FIG. 1) includes a swivel member 62, a vertical member 64, a support member 66, a horizontal member 68, and a gimbal 70. The swivel member 62 is rotatably supported on a base 61. The control arms 60 of the user interface 40 may each be supported on the same base 61 or each of the control arms 60 of a user interface 40 may be supported on a separate base 61. It is contemplated that the base 61 may be moveable (e.g., rolled) about a surgical environment before or after a surgical procedure and be fixed in position during a surgical procedure.

Figure 4:
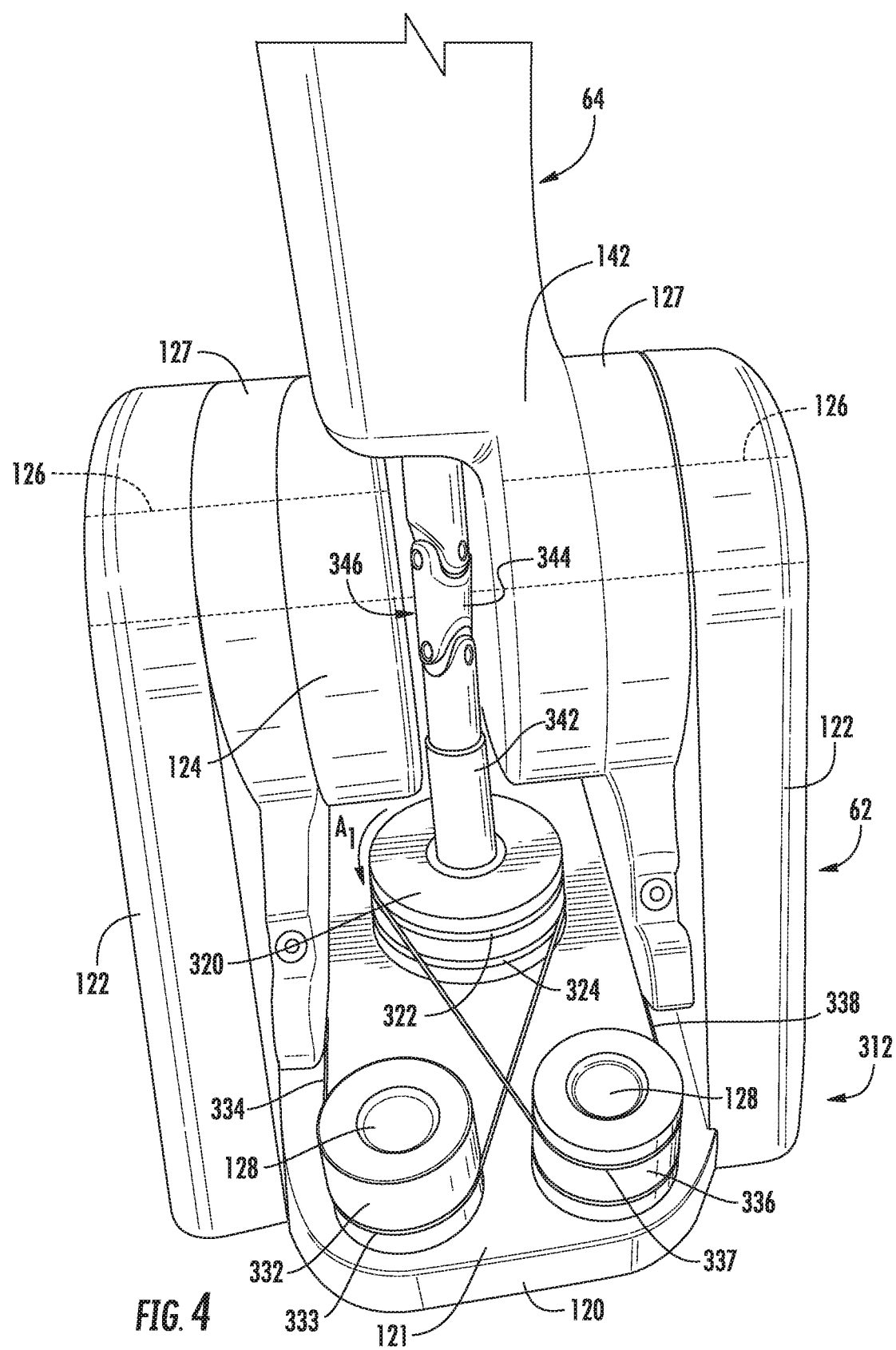
FIG. 4 is an enlarged perspective view of a lower portion of a vertical member of the control arm of FIG. 3.

With additional reference to FIG. 4, the swivel member 62 includes a bottom plate 120, flanges 122, a coupling member 124, lower pins 126, and posts 128. The flanges 122 extend vertically from each side of the bottom plate 120. Each of the flanges 122 defines a pin opening 123 that receives an outer end of one of the lower pins 126. A pin support 127 is positioned adjacent each of the flanges 122 to rotatably support a central portion of a respective lower pin 126. An inner end of one of the lower pins 126 rotatably supports the coupling member 124 and the inner end of the other lower pin 126 rotatably supports a lower end 142 of the vertical member 64. The coupling member 124 includes a finger 125 that extends from the lower pin 126 a distance $D_1$. The posts 128 extend vertically from the bottom plate 120 between the flanges 122. The coupling member 124 and the lower end 142 of the vertical member 64 may frictionally engage a respective one of the lower pins 126 such that the coupling member 124 and the lower end 142 are rotatable about the lower pins 126 in response to an external input or force but resist rotation about the lower pins 126 absent an external input.

Figure 5:
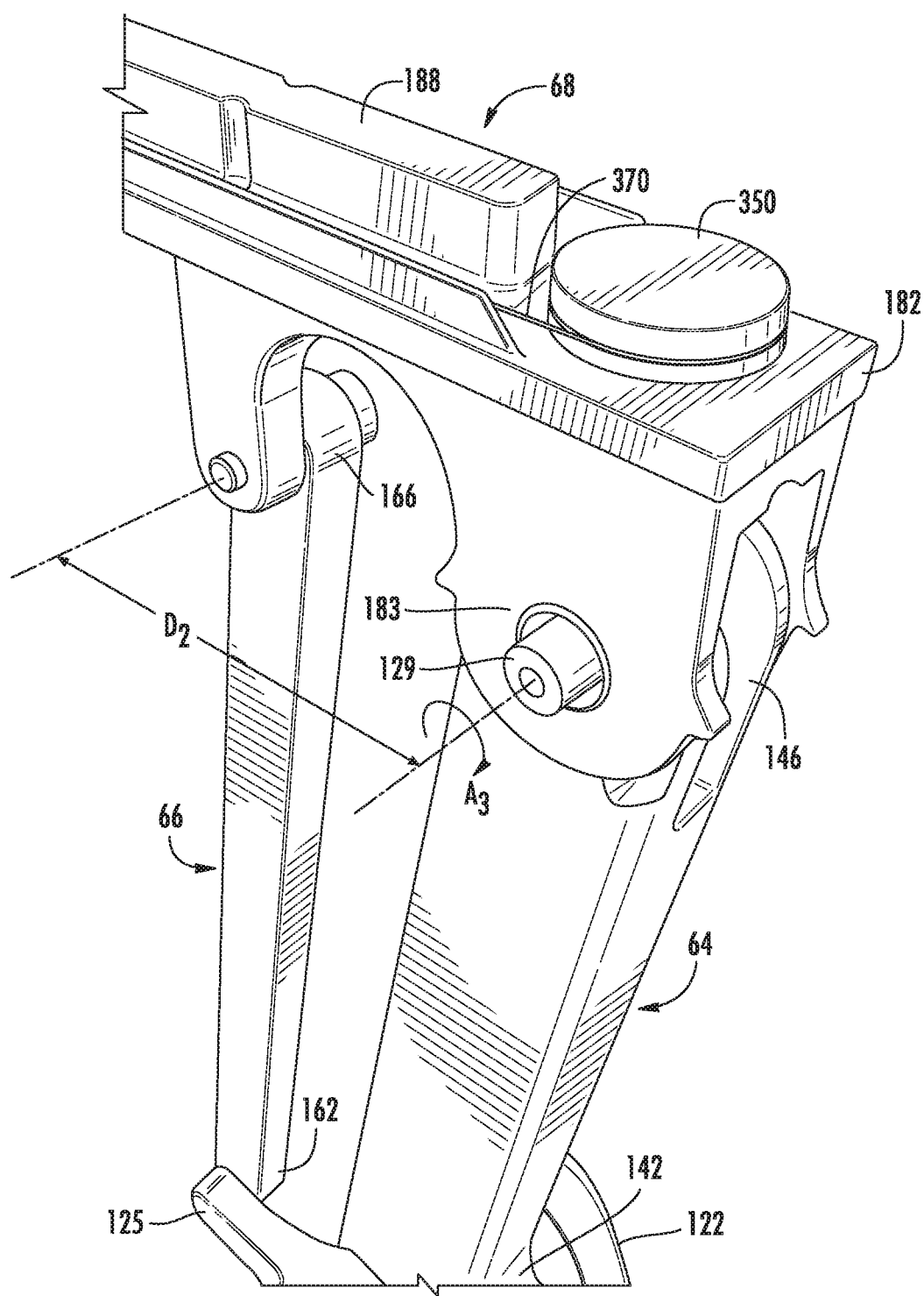
FIG. 5 is an enlarged perspective view of an upper portion of the vertical member of the control arm of FIG. 3.

Referring also to FIG. 5, the vertical member 64 extends vertically from the lower end 142. The vertical member 64 has an upper end 146 that is rotatably coupled to a distal tab 183 which is disposed at a first end 182 of the horizontal member 68 by upper pins 129. The support member 66 extends vertically from the lower end 162 which is rotatably supported by the finger 125 of the coupling member 124. The support member 66 has an upper end 166 that is rotatably coupled to a support tab 184 of the horizontal member 68 and offset from the center of the upper pins 129 a distance $D_2$. The distances $D_1$ and $D_2$ are substantially equal to one another such that the support member 66 is maintained in a substantially parallel relationship with the vertical member 64 as the control arm 60 is manipulated.

As illustrated in FIG. 3, the horizontal member 68 extends from the first end 182 to a second end 186 thereof. The horizontal member 68 includes a rib 188 disposed along a centerline thereof between the first and second ends 182, 186. The second end 186 of the horizontal member 68 rotatably supports the gimbal 70 as shown in FIG. 3.

With particular reference to FIG. 3, the gimbal 70 includes a support arm 72, a swing arm 74, an input support arm 76, and an input shaft 78. Each of the support, swing, and support arms 72, 74, 76 are L-shaped having a horizontal portion and a vertical portion as detailed below. The support, swing, and support arms 72, 74, 76 are sized such that the arms 72, 74, 76 may nest within each other when aligned in a single plane with the input support arm 76 nested in the swing arm 74 which is nested in the support arm 72. The input shaft 78 is engagable with an adaptor or input device (not shown) to control functions of a tool 20 (FIG. 1) of the robotic system 10.

Figure 6:
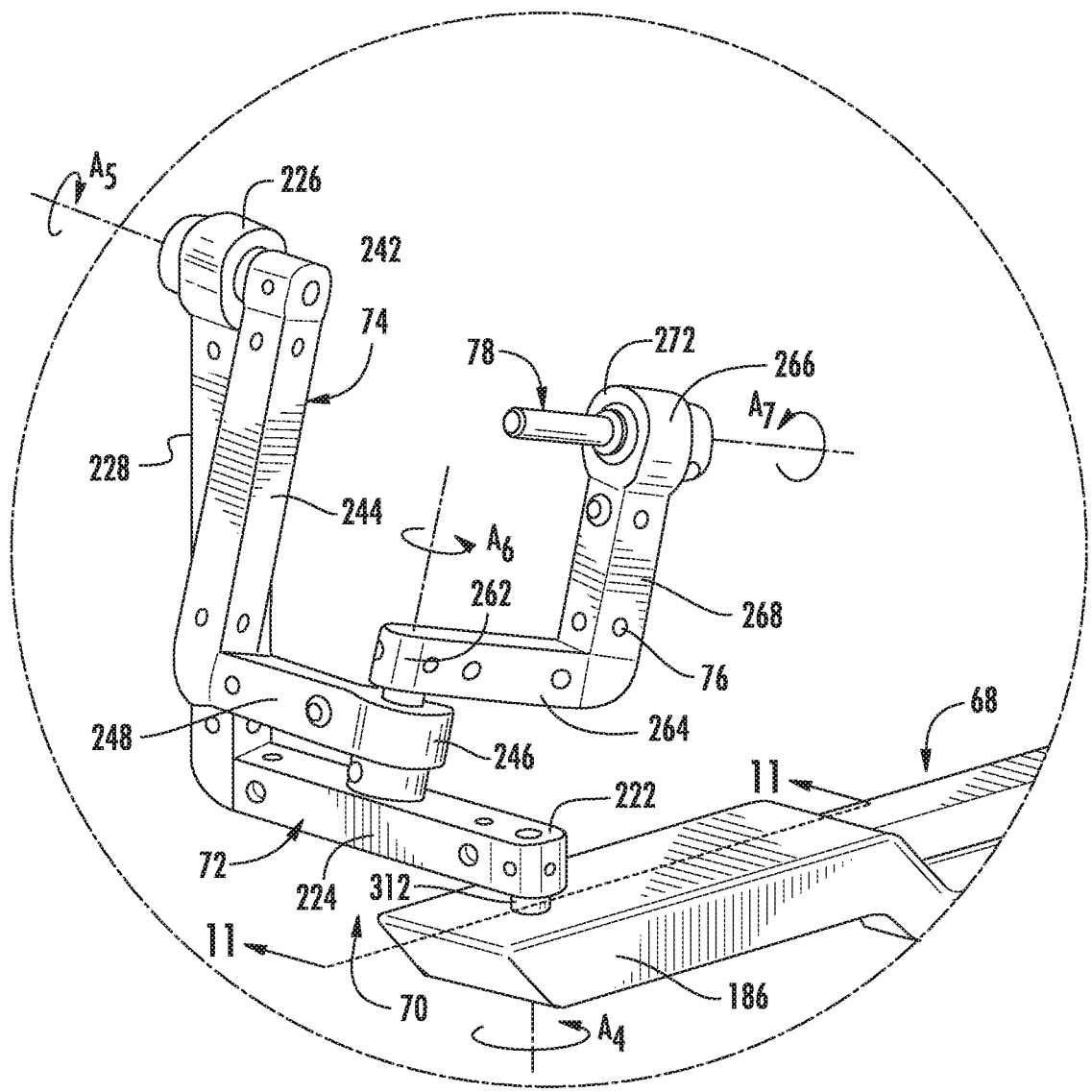
FIG. 6 is an enlarged view of the indicated area of detail of FIG. 3.

Referring to FIG. 6, the support arm 72 is rotatably coupled at a first end 222 to the second end 186 of the horizontal member 68. The support arm 72 is rotatably coupled at a second end 226 to a first end 242 of the swing arm 74. The support arm 72 has a horizontal portion 224 extending from its first end 222 that is orthogonal to a vertical portion 228 that extends from its second end 226. Similarly, the swing arm 74 has a vertical portion 244 that extends from its first end 242 that is orthogonal to a horizontal portion 248 that extends from its second end 246. The input support arm 76 is rotatably supported at its first end 262 by the second end 246 of the swing arm 74 and rotatably supports a first end 282 of the input shaft 78 at its second end 266. The input support arm 76 has a horizontal portion 264 that extends from its first end 262 that is orthogonal to a vertical portion 268 that extends from its second end 266.

Referring back to FIG. 3, the control arm 60 is rotatable about seven axes of rotation in response to a clinician interfacing with the gimbal 70 (e.g., interfacing with an input device disposed on the input shaft 78). Movement of the control arm 60 about the seven axes of rotation is detected by the processing unit 30 (FIG. 1) to manipulate the linkages 12 and tools 20 of the robotic surgical system 10. The construction of the control arm 60 and gimbal 70 limits movement of the respective members and linkages to rotation about the seven axes of rotation as detailed below.

The swivel member 62 is confined to rotation about a first axis of rotation $A_1$ with respect to the base 61. The lower end 142 of the vertical member 64 is confined to rotation about a second axis of rotation $A_2$ that is coincident with an axis defined by the lower pins 126. The second axis of rotation $A_2$ is substantially orthogonal to the first axis of rotation $A_1$. The first end 182 of the horizontal member 68 is confined to rotation relative to the upper end 146 of the vertical member 64 about a third axis of rotation $A_3$ that is coincident with an axis defined by the upper pins 129. The third axis of rotation $A_3$ is substantially parallel to the second axis of rotation $A_2$ and orthogonal to the first axis of rotation $A_1$. The first end 222 of the support arm 72 is rotatably supported on the second end 186 of the horizontal member 68 about a fourth axis of rotation $A_4$ which is coincident with an axis defined by a gimbal shaft 362. The first end 242 of the swing arm 74 is rotatably supported by the second end 226 of the swing arm 76 about a fifth axis of rotation $A_5$. The first end 262 of the input support arm 76 is rotatably supported by the second end 246 of the swing arm 74 about a sixth axis of rotation $A_6$. The first end 282 of the input shaft 78 is rotatably supported by the second end 266 of the input support arm 76 about a seventh axis of rotation $A_7$.

Referring now to FIGS. 3, 4, and 7-11, a passive axis system 300 is disclosed in accordance with the present disclosure to correlate rotation of the swivel member 62 about the first axis of rotation $A_1$ with rotation of the gimbal 70 about the fourth axis of rotation $A_4$. Specifically, the passive axis system 300 correlates rotation of the swivel member 62 relative to the base 61 to rotation of the first end 222 of the support arm 72 of the gimbal 70 relative to the second end 186 of the horizontal member 68 about the fourth axis of rotation $A_4$.

With particular reference to FIG. 4, the passive axis system 300 includes a first pulley assembly 312 disposed on an upper surface of the bottom plate 120 of the swivel member 62. The first pulley assembly 312 includes a first pulley 320, a first idler cylinder 332, a second idler cylinder 336, a first lower cord 334, and a second lower cord 338. The first pulley 320 is positioned adjacent an upper surface 121 of the bottom plate 120 such that the first pulley 320 is rotatable about the first axis of rotation $A_1$ relative to the swivel member 62. The first pulley 320 defines an upper circumferential groove 322 and a lower circumferential groove 324. It will be appreciated that the first axis of rotation $A_1$ is orthogonal to a plane defined by the upper surface 121 of the bottom plate 120. The first and second idler cylinders 332, 336 are disposed over and rotatable about the posts 128. Each of the first and second idler cylinders 332, 336 defines a circumferential groove 333, 337, respectively. The first lower cord 334 is attached at one end to one of the pin supports 127, within the circumferential groove 333 around the first idler cylinder 332, and into the lower circumferential groove 324 of the first pulley 320 where the other end of the first lower cord 334 is attached to the first pulley 320. The second lower cord 338 is attached at one end to the other one of the pin supports 127, within the circumferential groove 337 around the second idler cylinder 336, and into the upper circumferential groove 322 of the first pulley where the other end of the second lower cord 338 is attached to the first pulley 320.

The first pulley assembly 312 rotates the first pulley 320 relative to the swivel member 62 as the swivel member 62 is rotated relative to the base 61 about the first axis of rotation $A_1$. Specifically, as the swivel member 62 is rotated about the first axis of rotation $A_1$, the first and second idler cylinders 332, 336 are rotated about the first pulley 320 such that the first and second lower cords 334, 338 rotate the first pulley 320 relative to the swivel member 62. More specifically, first and second lower cords 334, 338 maintain the first pulley 320 in position relative to the base 61 while the swivel member 62 is rotated relative to the base 61.

Figure 7:
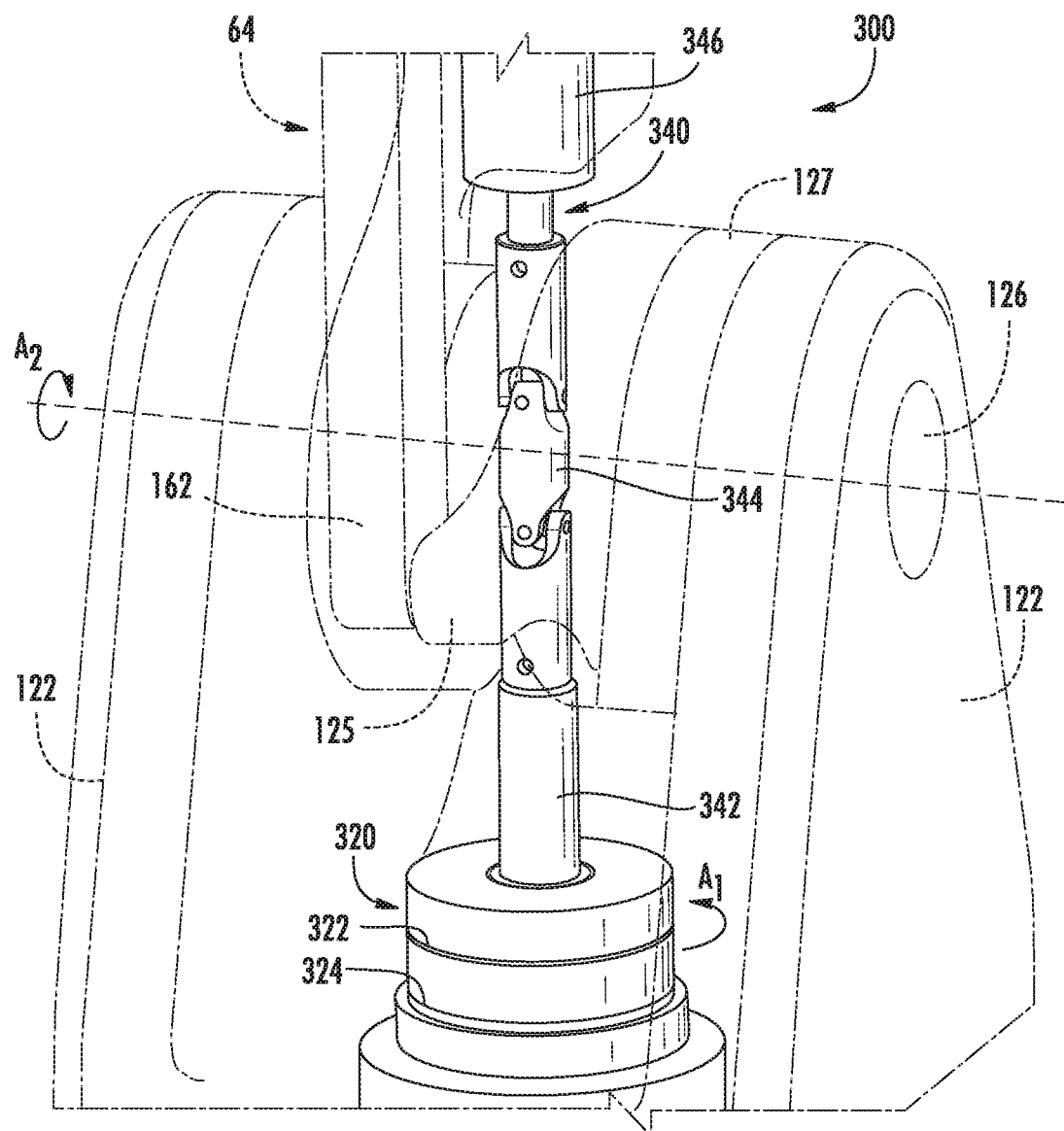
FIG. 7 is an enlarged perspective view of a lower pulley assembly of a passive axis system of FIG. 3.
Figure 8:
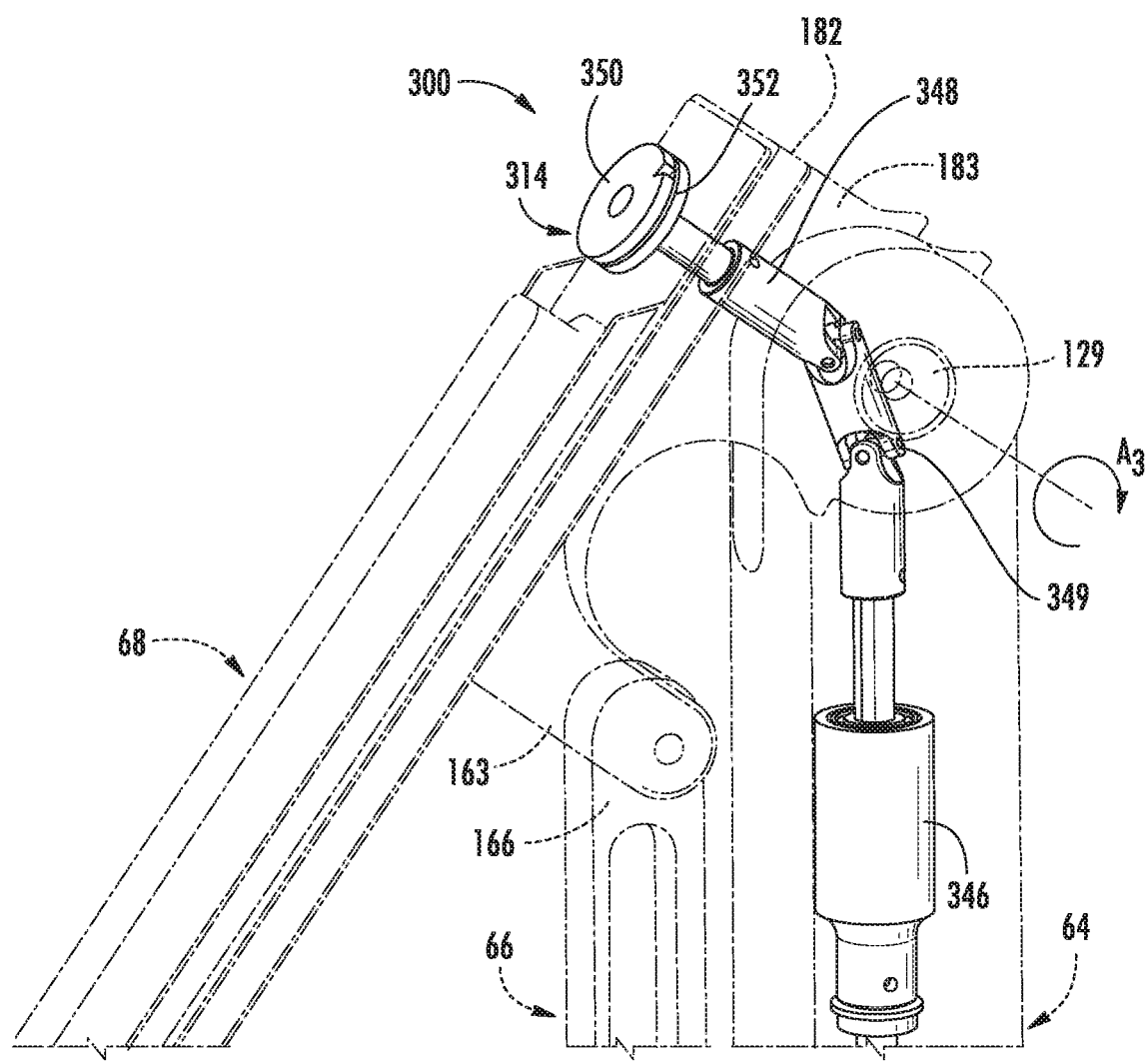
FIG. 8 is an enlarged perspective view of a portion of an upper pulley assembly of the passive axis system.
Figure 9:
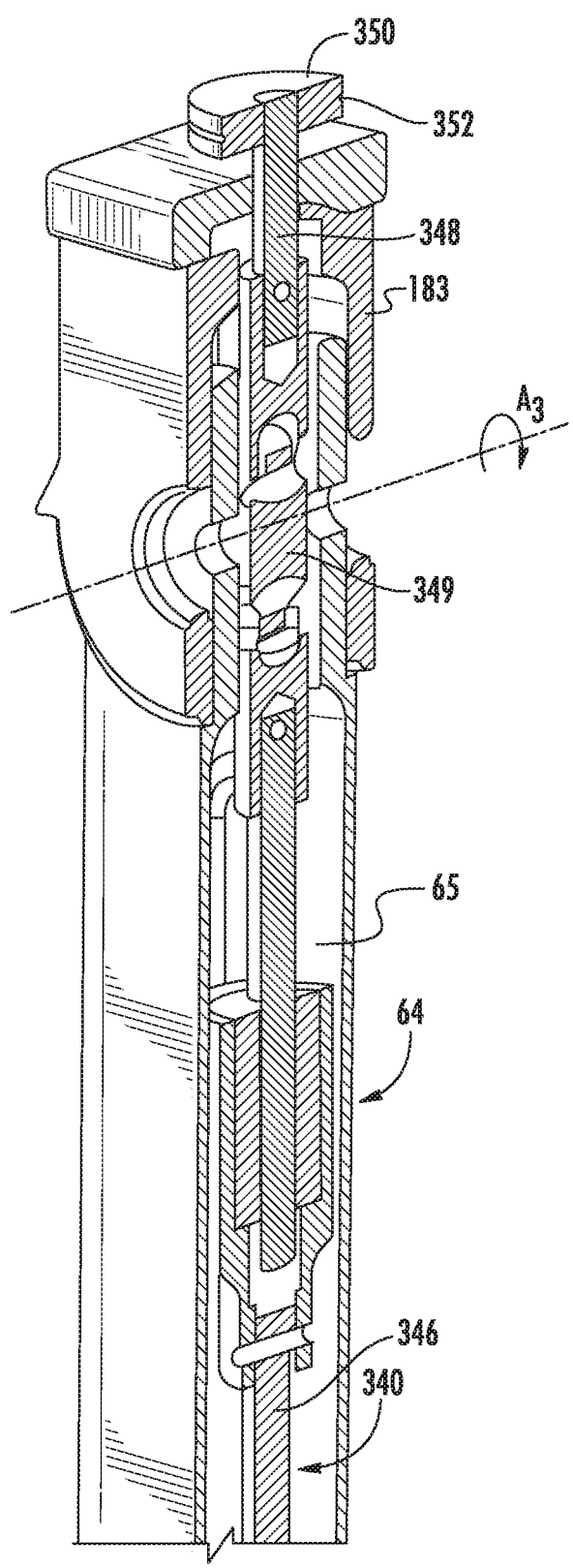
FIG. 9 is a cross-sectional view taken along the section line 9-9 of FIG. 3.

With reference to FIGS. 7-9, the passive axis system 300 includes a connecting shaft 340 and an upper pulley 350. The connecting shaft 340 is disposed within a lumen 65 defined within the vertical member 64 and rotatably couples the lower pulley assembly 320 to the upper pulley 350 as detailed below.

The connecting shaft 340 has a lower portion 342, a central portion 346, and an upper portion 348. The lower portion 342 is coupled to the central portion 346 by a lower universal joint 344 and the upper portion 348 is coupled to the central portion 346 by an upper universal joint 349. It is contemplated that the lower and upper universal joints 344, 349 are exemplary and that suitable flexible shafts, hydraulic systems, pneumatic systems, or cable driven systems could be used in place of one or both of the lower and upper universal joints 344, 349. The lower portion 342 is rotatably fixed to the lower pulley assembly 320 such that the connecting shaft 340 is rotatably fixed to the lower pulley assembly 320. Specifically, an end of the lower portion 342 is disposed within a central opening defined by the lower pulley assembly 320. The lower universal joint 344 is positioned such that the second axis of rotation $A_2$ passes through the lower universal joint 344. The positioning of the lower universal joint 344 allows rotation of the vertical member 64 about the second axis of rotation $A_2$ without affecting rotation of the connecting shaft 340. The upper universal joint 349 is positioned such that the third axis of rotation $A_3$ passes through the upper universal joint 349. The positioning of the upper universal joint 349 allows rotation of the horizontal member 68 relative to the vertical member 64 about the third axis of rotation $A_3$ without affecting rotation of the connecting shaft 340. The upper pulley 350 is positioned adjacent an upper surface 181 of the horizontal member 68 such that a plane defined by the upper pulley 350 is substantially parallel to the upper surface 181 of the horizontal member 68.

Figure 10:
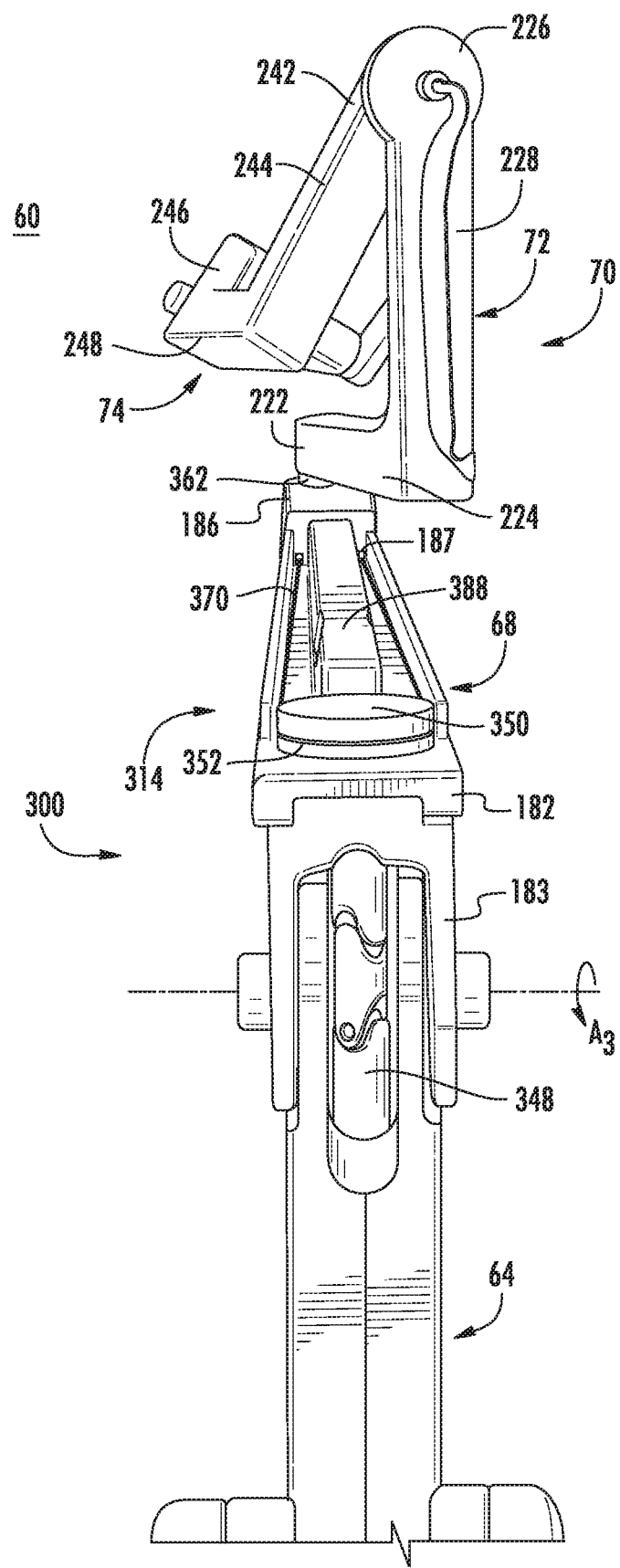
FIG. 10 is a rear perspective view of the control arm of FIG. 3.
Figure 11:
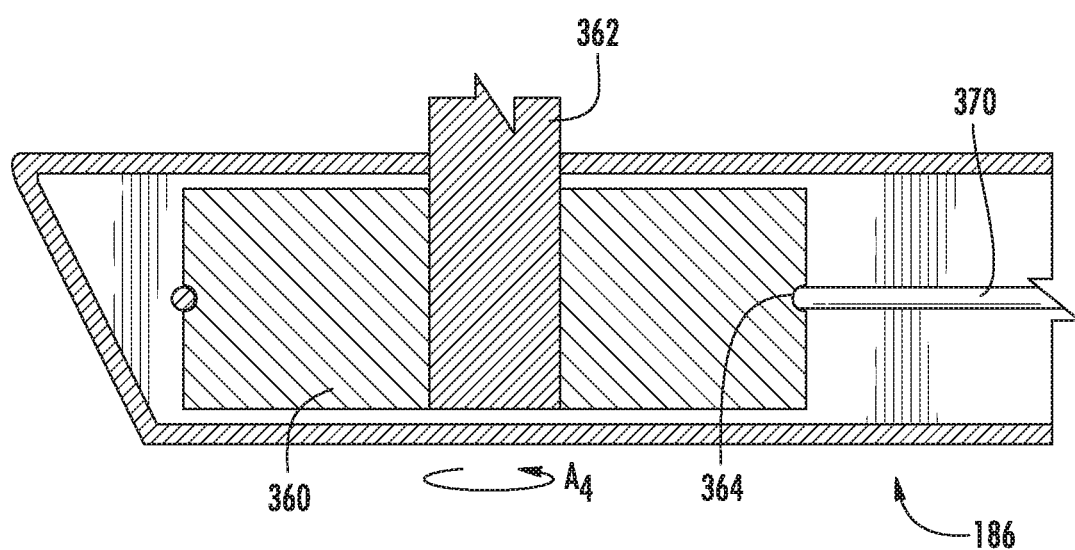
FIG. 11 is a cross-sectional view taken along the section line 11-11 of FIG. 6.

Referring now to FIGS. 10 and 11, the passive axis system 300 also includes an upper pulley assembly 314 that is configured to rotate the gimbal 70 relative to the horizontal member 68 about the fourth axis of rotation $A_4$ in response to rotation of the upper pulley 350. The upper pulley assembly 314 includes the upper pulley 350, a gimbal pulley 360 and an upper cable 370. The gimbal pulley 360 is disposed within the second end 186 of the horizontal member 68 and is connected to the gimbal 70 by a gimbal shaft 362. The gimbal shaft 362 is rotatably fixed to the gimbal pulley 360 and the first end 272 of the support arm 72 of the gimbal 70 such that as the gimbal pulley 360 is rotated about the fourth axis of rotation $A_4$, the support arm 72 is rotated about the first end 272. It will be appreciated that the forth axis of rotation $A_4$ is defined by the gimbal shaft 362. The upper pulley 350 is operably associated with the gimbal pulley 360 by the upper cable 370. The upper pulley 350 defines a circumferential groove 352 and the gimbal pulley 360 defines a circumferential groove 364 which each receiving the upper cable 370. The upper cable 370 is tensioned about the upper pulley 350 and gimbal pulley 360 such that as the upper pulley 350 is rotated, the gimbal pulley 360 is rotated an equal radial distance in the same radial direction. It is contemplated that the upper pulley 350 and the gimbal pulley 360 may be sized such that rotation of the gimbal pulley 360 is greater or less than the rotation of the upper pulley 350.

With particular reference to FIG. 10, the second end 186 of the horizontal member 68 defines cable passages 187 that allow the upper cable 370 to pass through the second end 186 and around the gimbal pulley 360. By placing the gimbal pulley 360 within the second end 186 of the horizontal member 68, the gimbal pulley 360 is shielded from incidental contact with a clinician interfacing with the gimbal 70. It is contemplated that the rib 388 may define a cable passage (not shown) such that the upper cable 370 may cross through the rib 388 such that rotation of the gimbal pulley 360 is in the opposite direction relative to the rotation of the upper pulley 350.

Figure 12C:
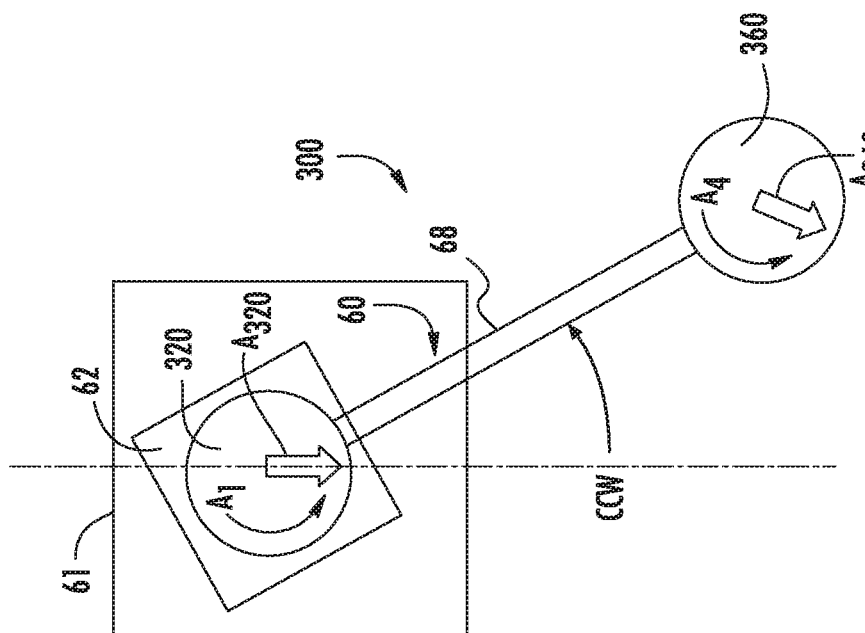
FIGS. 12A-C are schematic illustrations of the passive axis system correlating rotation of a first pulley with rotation of a gimbal pulley.
Figure 12B:
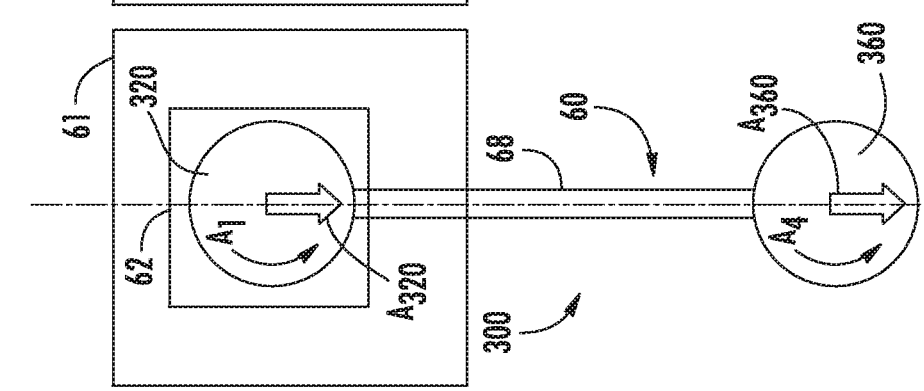
Figure 12A:
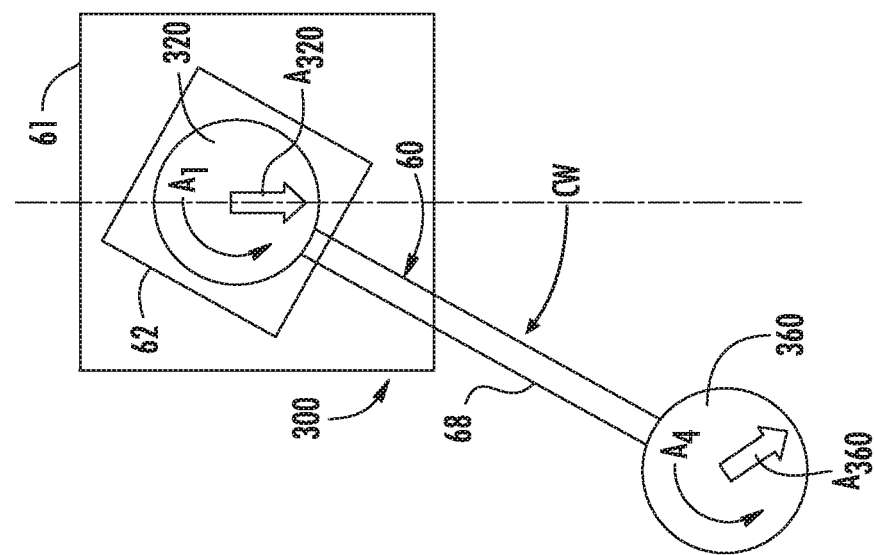

Referring now to FIGS. 12A-C, the passive axis system 300 correlates rotation of the control arm 60 about the first axis of rotation $A_1$ with rotation of the gimbal pulley 360 about the fourth axis of rotation $A_4$ such that rotation of the gimbal pulley 360 is opposite the rotation of the control arm 60. As shown in FIG. 12A, when the control arm 60 is rotated in a clockwise direction, as indicated by arrow CW from a neutral position (FIG. 12B), the lower pulley assembly 320, as indicated with directional arrow $A_{320}$, remains stationary such that the lower pulley assembly 320 rotates relative to the swivel member 62. The rotation of the lower pulley assembly 320 relative to the swivel member 62 rotates the gimbal pulley 360, as indicated with directional arrow $A_{360}$, an angular distance equal to the rotation of the lower pulley assembly 320 relative to the swivel member 62 in an opposite direction (i.e., counter clockwise). Similarly as shown in FIG. 12C, when the control arm 60 is rotated in a counter clockwise direction, as indicated by arrow CCW from a neutral position (FIG. 12B), the lower pulley assembly 320, as indicated with the directional arrow $A_{320}$, remains stationary such that the lower pulley assembly 320 rotates relative to the swivel member 62. The rotation of the lower pulley assembly 320 relative to the swivel member 62 rotates the gimbal pulley 360, as indicated with directional arrow $A_{360}$, an angular distance scaled to the rotation of the lower pulley assembly 320 relative to the swivel member 62 in an opposite direction (i.e., clockwise). The scaling of the angular distance of rotation of gimbal pulley 360 may be scaled to rotation of the lower pulley in a range of about 0.5 to about 1.0 (e.g., about 0.7).

With reference to FIGS. 13A-C, the input shaft 78 of the gimbal 70 is engaged to rotate the control arm 60 about the first axis of rotation $A_1$ from a neutral position (FIG. 12B) to a first position (FIG. 13A) and to a second position (FIG. 13C). As the control arm 60 is rotated, the passive axis system 300 rotates the support arm 72 of the gimbal 70 about the fourth axis of rotation $A_4$ to maintain an angle $\theta$ defined between the support arm 72 and the input shaft 78. Specifically, the passive axis system 300 maintains the position of the upper pulley 350 with the lower pulley assembly 320, as represented by Arrows $A_{350}$ and $A_{320}$, respectively, and correlates the rotation of the lower pulley assembly 320 with rotation of the arm 72 as indicated by Arrow $A_{72}$. For example, when the control arm 60 is rotated in a clockwise direction about the first axis of rotation $A_1$, to the first position (FIG. 13A), the passive axis system 300 rotates the support arm 72 of the gimbal 70 in a counter clockwise direction about the fourth axis of rotation $A_4$, to maintain the angle $\theta$ between the support arm 72 and the input shaft 78. Likewise, when the control arm 60 is rotated in a counter clockwise direction about the first axis of rotation $A_1$, to a second position (FIG. 13B), the passive axis system 300 rotates the support arm 72 of the gimbal 70 about the fourth axis of rotation $A_4$, to maintain the angle $\theta$ between the support arm 72 and the input shaft 78. It will be appreciated that as the control arm 60 is rotated a first angular distance in a first direction about the first axis of rotation $A_1$, the passive axis system 300 rotates the support arm 72 the first angular distance in a second direction which is opposite the first direction about the fourth axis of rotation $A_4$.

In FIGS. 13A-C, the vertical member 64 (FIG. 3) is substantially vertical and the horizontal member 68 (FIG. 3) is substantially horizontal. However, it will be appreciated that the passive axis system 300 functions when the vertical member 64 is off-set from a vertical plane (i.e., rotated about the second axis of rotation $A_2$) and when the horizontal member 68 is offset from a horizontal plane (i.e., when the vertical member 64 is rotated about the second axis of rotation $A_2$ and/or when the horizontal member 68 is rotated about the third axis of rotation $A_3$).

Therefore, including a passive axis system (e.g., passive axis system 300 as detailed above) to induce rotation of the support arm 72 of the gimbal 70 as the control arm 60 is rotated, reduces the likelihood that the arms 72, 74, 76 of the gimbal 70 will splay or nest with one another and thus, prevents the degrees-of-freedom of movement of the gimbal 70 from being reduced. In addition, as detailed above, the passive axis system 300 is disposed substantially within the vertical member 64 and horizontal member 68 to prevent incidental contact with moving elements of the passive axis system 300 (e.g., connecting shaft 340). In addition, it is contemplated that the swivel member 62 includes a cover (not shown) to shield or encapsulate the lower pulley assembly 312 (e.g., the lower pulley assembly 320 and the idler cylinders 332, 336). Further, it is contemplated, that the horizontal member 68 may include a cover (not shown) to fully cover or shield the upper cable assembly 314 (e.g., the cable 370 and the upper pulley 350).

As detailed herein, the passive axis system utilizes cords 334, 338, shaft 340, and wire loop 370 to associate the first axis with the fourth axis, however, it is contemplated that other methods (e.g., gears, hydraulics, cable-conduit drives, torsion tubes, etc.) may be utilized to associate the first axis with the fourth axis.

Figure 14:
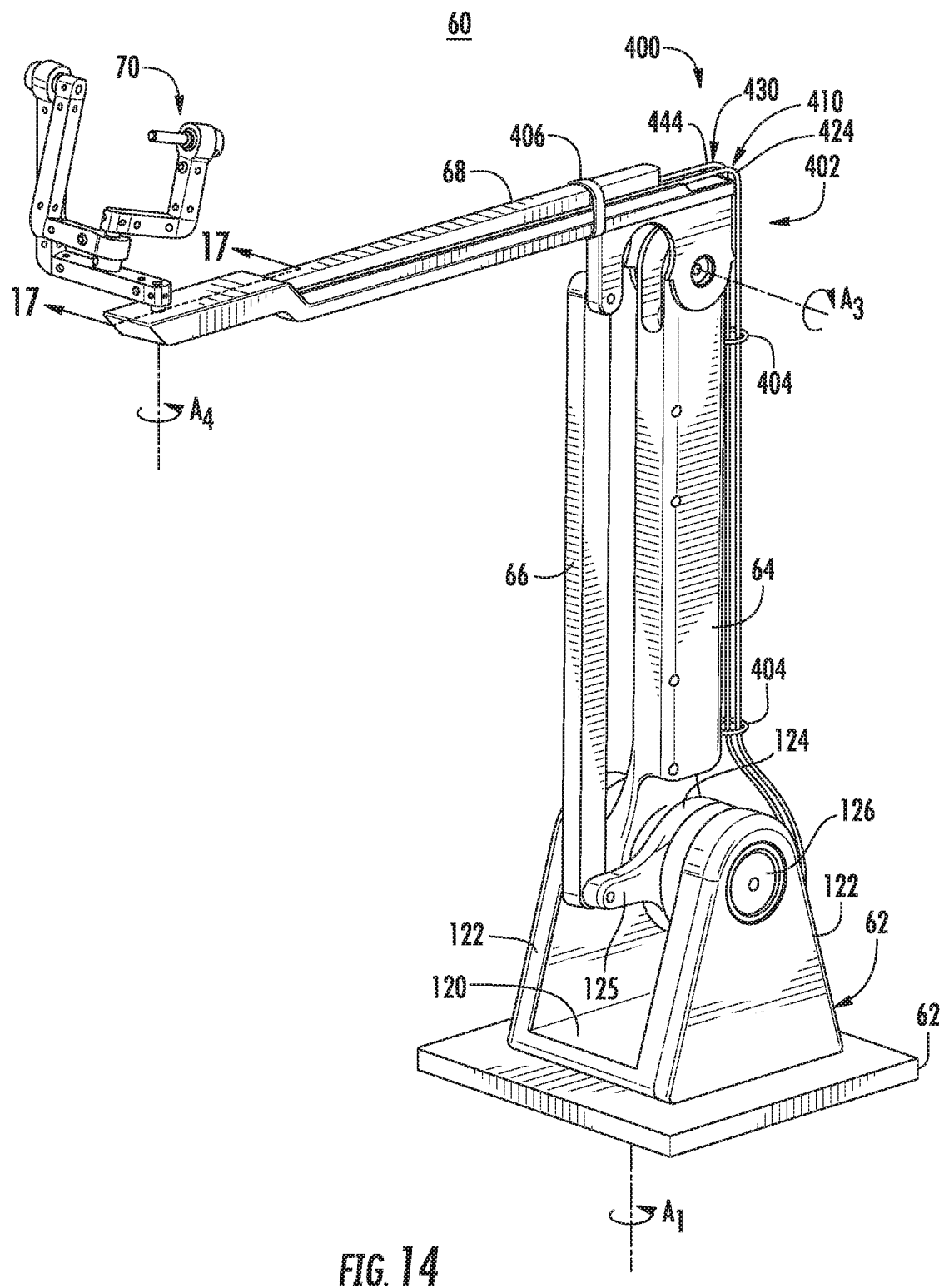
FIG. 14 is a perspective view of the control arm of the user interface of FIG. 1 including another passive axis system provided in accordance with the present disclosure.
Figure 15:
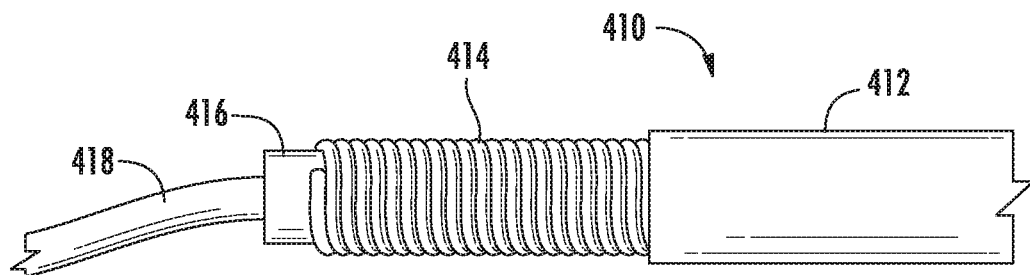
FIG. 15 is an enlarged view of a pull cable of the passive axis system of FIG. 14.

Referring now to FIGS. 14 and 15, a passive axis system 400 is disclosed in accordance with the present disclosure including a cable-conduit drive system 402 to associate the first axis $A_1$ of rotation of the control arm 60 with the fourth axis of rotation $A_4$ of the gimbal 70. The cable-conduit drive system 402 includes a first cable-conduit 410 and a second cable-conduit 430. As shown in FIG. 15, the first cable-conduit 410 includes, from outside in, an outer cover 412, a wound spring 414, a liner 416, and an actuation cable 418. The outer cover 412 is constructed from a flexible material that is configured to protect the wound spring 414 and the actuation cable 418. The wound spring 414 is configured to provide rigidity to the first cable-conduit 410 while allowing the first cable-conduit 410 to resiliently flex in response to movement of the control arm 60 as detailed below. The wound spring 414 may also be flexed beyond resiliency during assembly or manufacturing such that the first cable-conduit 410 has a bend or a corner (e.g., bend 424) while permitting the actuation cable 418 to freely slide within the first cable-conduit 410 as detailed below. The liner 416 is disposed within the wound spring 414 to reduce friction for sliding or actuating the actuation cable 418 within the first cable-conduit 410. The liner 416 may be formed from polytetrafluoroethylene (PTFE), commercially available as Teflon®. The second cable-conduit 430 is constructed in a similar manner to the first cable-conduit 410, as such, the construction of the second cable-conduit 430 will not be detailed herein for reasons of brevity.

Figure 17:
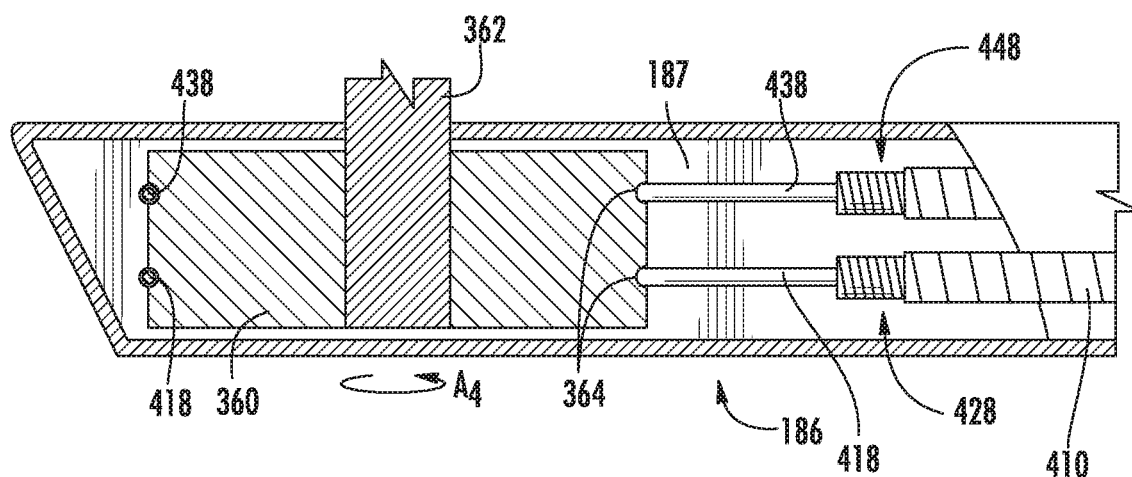
FIG. 17 is a cross-sectional view taken along section line 17-17 of FIG. 14.
Figure 16:
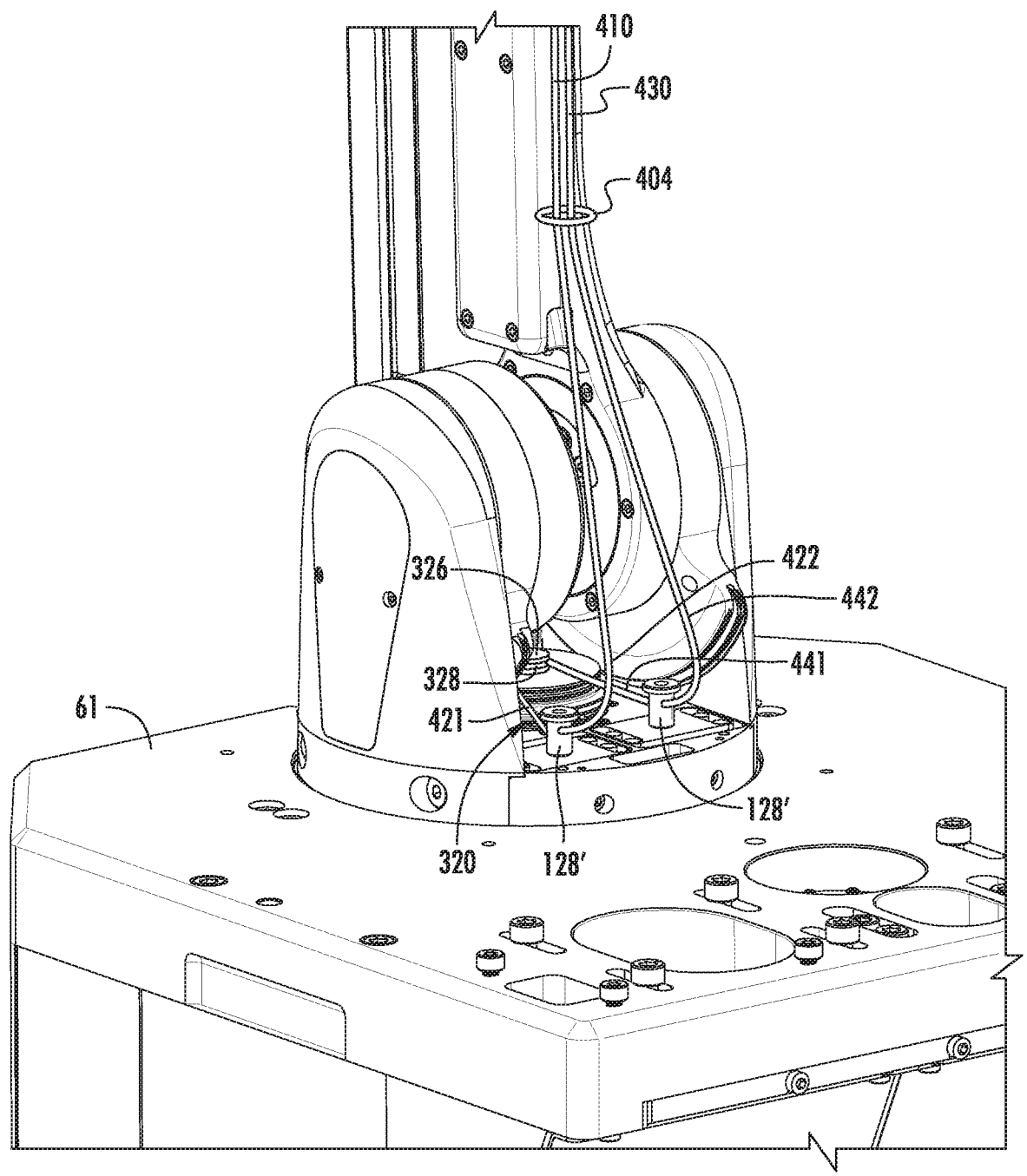
FIG. 16 is a rear perspective view of a lower portion of the control arm of FIG. 14.

With additional reference to FIGS. 16 and 17, the first cable-conduit 410 includes a lower portion 422 that is operably associated with the lower pulley assembly 320 supported on the swivel member 62 of the control arm 60 and an upper portion 428 that is operably associated with the gimbal pulley 360 (FIG. 11). Specifically, the lower portion 422 of the first cable-conduit 410 is fixed to the swivel member 62 such that a first end 421 of the actuation cable 418 extends from the liner 416 and is positioned within a groove 328 defined in a pulley 326 or the lower pulley assembly 320 positioned about the first axis of rotation $A_1$. The remainder of the lower portion 422 (the liner 416, the wound spring 414, and the cover 412) of the first cable-conduit 410 is secured to the swivel member 62 by a mount 128'.

Similarly, the second cable-conduit 430 includes a lower portion 442 that is operably associated with the pulley 326 supported on the swivel member 62 of the control arm 60 and an upper portion 448 that is operably associated with the gimbal pulley 360. Specifically, the lower portion 448 of the second cable-conduit 430 is fixed to the base 61 such that a first end 441 of an actuation cable 438 of the second cable-conduit 430 extends from a liner 436 and is positioned within the groove 328 defined in the pulley 326 positioned about the first axis of rotation $A_1$. The remainder of the lower portion 442 (the liner 436, the wound spring 434, and the cover 432) of the second cable-conduit 430 is secured to the swivel member 62 by a mount 128'.

The first and second cable-conduits 410, 430 extend from the mount 128' along the vertical member 64 and the horizontal member 68 to the gimbal pulley 360. As shown, the first and second cable-conduits 410, 430 extend along the outside of the vertical member 64. Additionally, the first and second cable-conduits 410, 430 may be secured to the outside vertical member 64 by securement member or eyelets 404. Alternatively, the first and second cable-conduits 410, 430 may pass through the lumen 65 (FIG. 9) defined within the vertical member 64.

As the first and second cable-conduits 410, 430 transition from extending along, or within, the vertical member 64, the first and second cable-conduits 410, 430 wrap around the third axis of rotation $A_3$ before extending along the horizontal member 68. The first and second cable-conduits 410, 430 each include a respective bend 424, 444 around the third axis of rotation $A_3$ between vertical member 64 and the horizontal member 68. The bends 424, 444 are formed by bending the respective one of the first and second cable-conduits 410, 430, beyond the resilience of the wound spring 414, 434, to form a curve in the respective one of the first and second cable-conduits 410, 430 such that the first and second cable-conduits 410, 430 resiliently flex when the horizontal member 68 pivots relative to the vertical member 64. The bends 424, 444 allow the first and second cable-conduits 410, 430 to comply with the pivoting horizontal member 68 relative to the vertical member 64 while reducing slack of the first and second cable-conduits 410, 430. Additionally, the first and second cable-conduits 410, 430 may be secured to the vertical member 64 adjacent the third axis of rotation $A_3$ by an eyelet 404 and/or may be secured to the horizontal member 68 adjacent the third axis of rotation $A_3$ by a strap 406 to reduce the slack in the first and second cable-conduits 410, 430.

The first cable-conduit 410 extends along the horizontal member 68 to the gimbal pulley 360. An upper portion 426 of the first cable-conduit 410 is secured to the horizontal member 68 adjacent the gimbal pulley 360 and a second end 428 of the first cable-conduit 410 is secured within a first circumferential groove 364 of the gimbal pulley 360. The remainder of the first cable-conduit 410 is fixed relative to the horizontal member 68 adjacent the gimbal pulley 360. It is contemplated that the liner 416, the wound spring 414, and the cover 412 of the first cable-conduit 410 may be securely fixed by walls defining the cable passage 187 engaging the first cable-conduit 410 while allowing the actuation cable 418 of the first cable-conduit 410 to freely slide relative to the horizontal member 68 to rotate the gimbal pulley 360 as detailed below.

The second cable-conduit 430 extends along the horizontal member 68 to the gimbal pulley 360. An upper portion 446 of the second cable-conduit 430 is secured to the horizontal member 68 adjacent the gimbal pulley 360 and a second end 448 of the second cable-conduit 430 is secured within a second circumferential groove 366 of the gimbal pulley 360. The remainder of the second cable-conduit 430 is fixed relative to the horizontal member 68 adjacent the gimbal pulley 360. It is contemplated that the liner 436, the wound spring 434, and the cover 432 of the second cable-conduit 430 may be securely fixed by walls defining the cable passage 187 engaging the second cable-conduit 430 while allowing the actuation cable 438 of the second cable-conduit 430 to freely slide relative to the horizontal member 68 to rotate the gimbal pulley 360.

Figure 18:
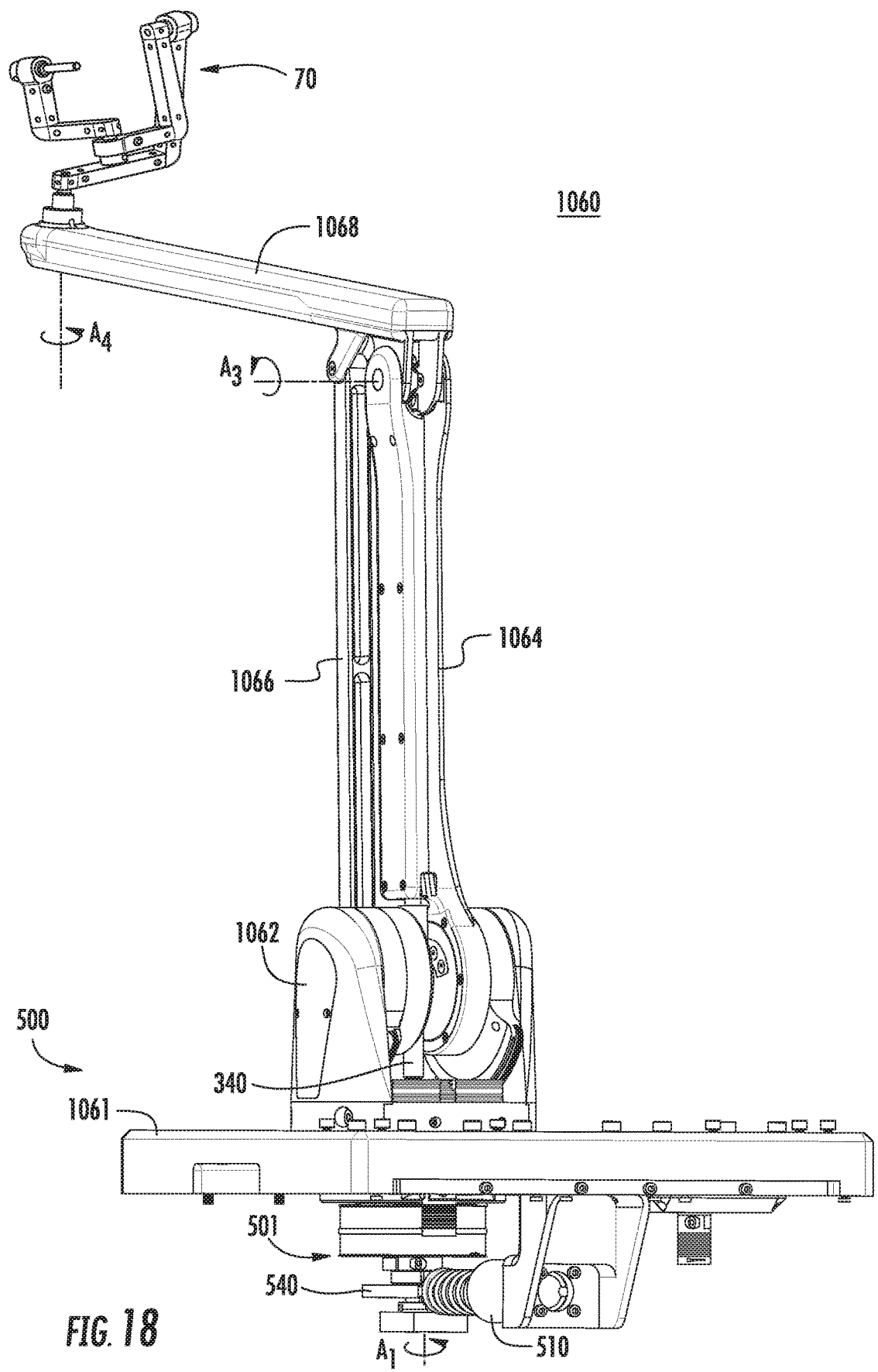
FIG. 18 is a perspective view of another control arm of the user interface of FIG. 1 provided in accordance with the present disclosure including a limit extending mechanism.
Figure 19:
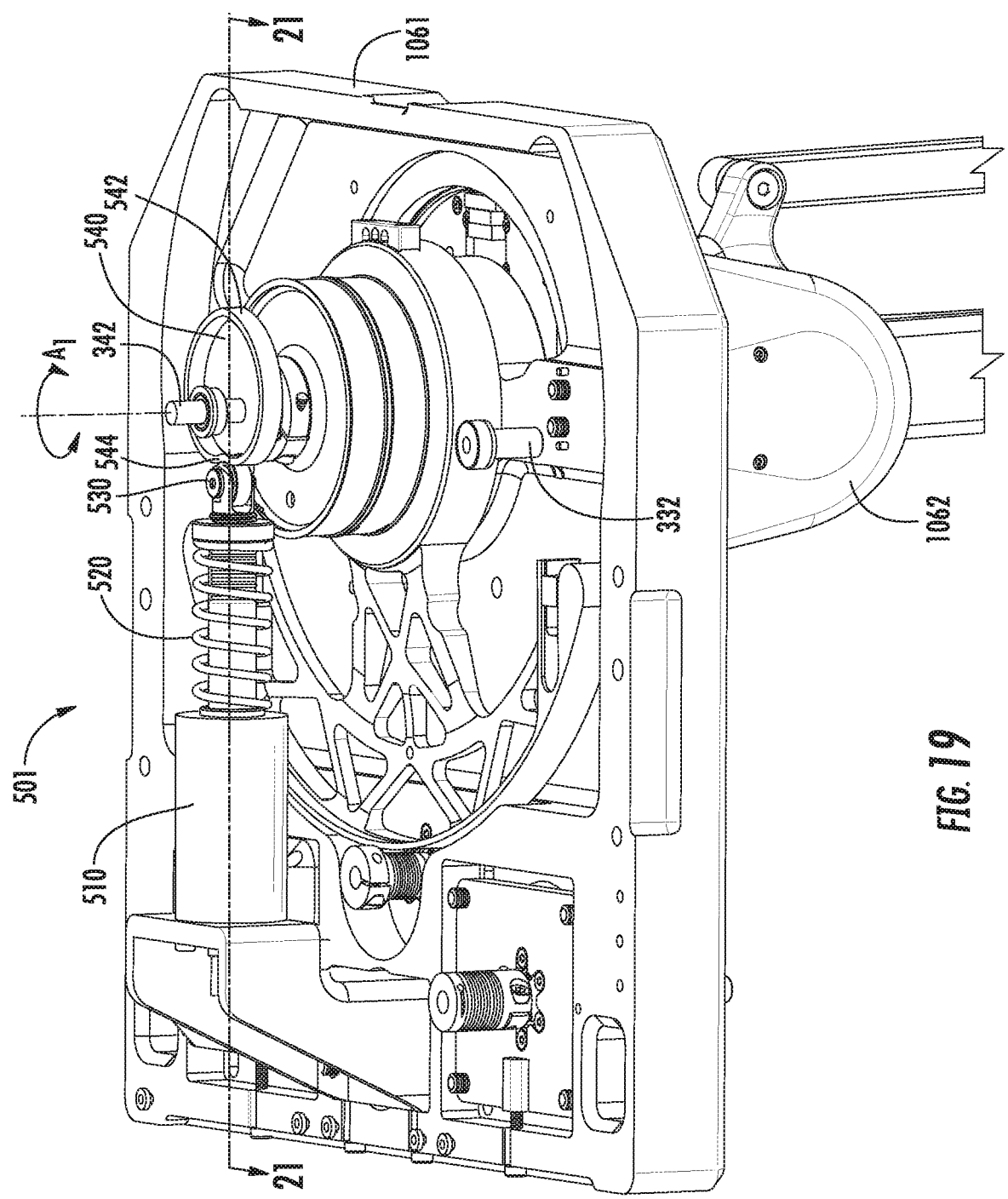
FIG. 19 is a bottom view of the limit extending mechanism of FIG. 18.
Figure 20:
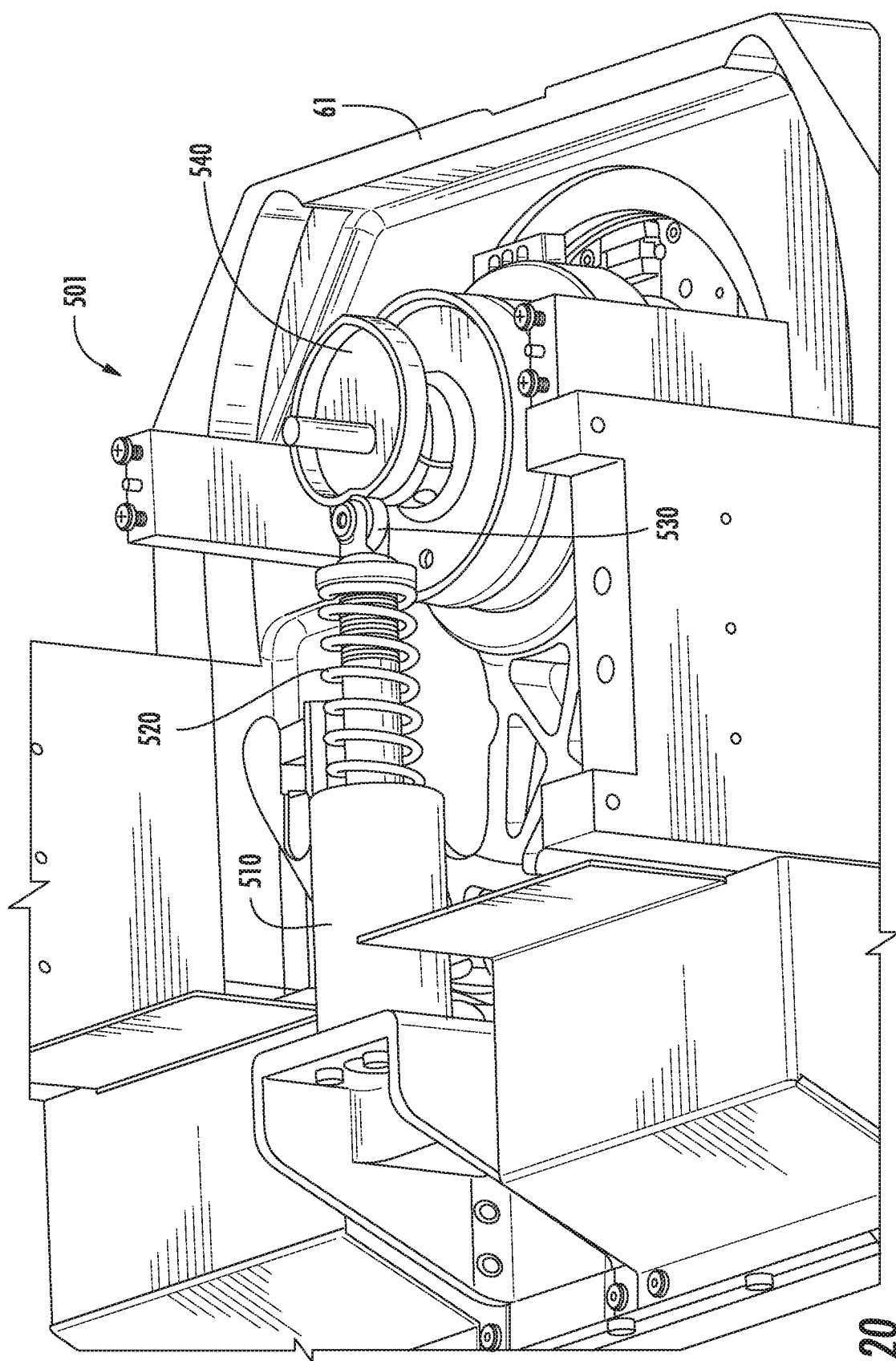
FIG. 20 is another bottom view of the limit extending mechanism of FIG. 18.

Referring to FIGS. 18-20, another control arm 1060 is disclosed in accordance with the present disclosure. The control arm 1060 is similar to control arm 60 described above with like elements labeled with a "10" preceding the previous label. The control arm 1060 includes a passive axis system 500 that associates rotation of a gimbal 70 about a fourth axis of rotation $A_4$ with rotation of a swivel member 1062 relative to a base 1061 about a first axis of rotation $A_1$.

Similar to the passive axis system 300 detailed above, the passive axis system 500 includes a connecting shaft 340 having a lower portion 342 that passes through the swivel member 1062 and the base 1061. The lower portion of the connecting shaft 340 is disposed about the first axis of rotation $A_1$ within the base 1061.

The passive axis system 500 includes a rotational limit extending mechanism 501 allows the gimbal 70 to rotate about the fourth axis of rotation $A_4$ independent of rotation of the swivel member 1062 relative to the base 1061 when the swivel member 1062 is at a threshold limit of rotation as detailed below.

Figure 21:
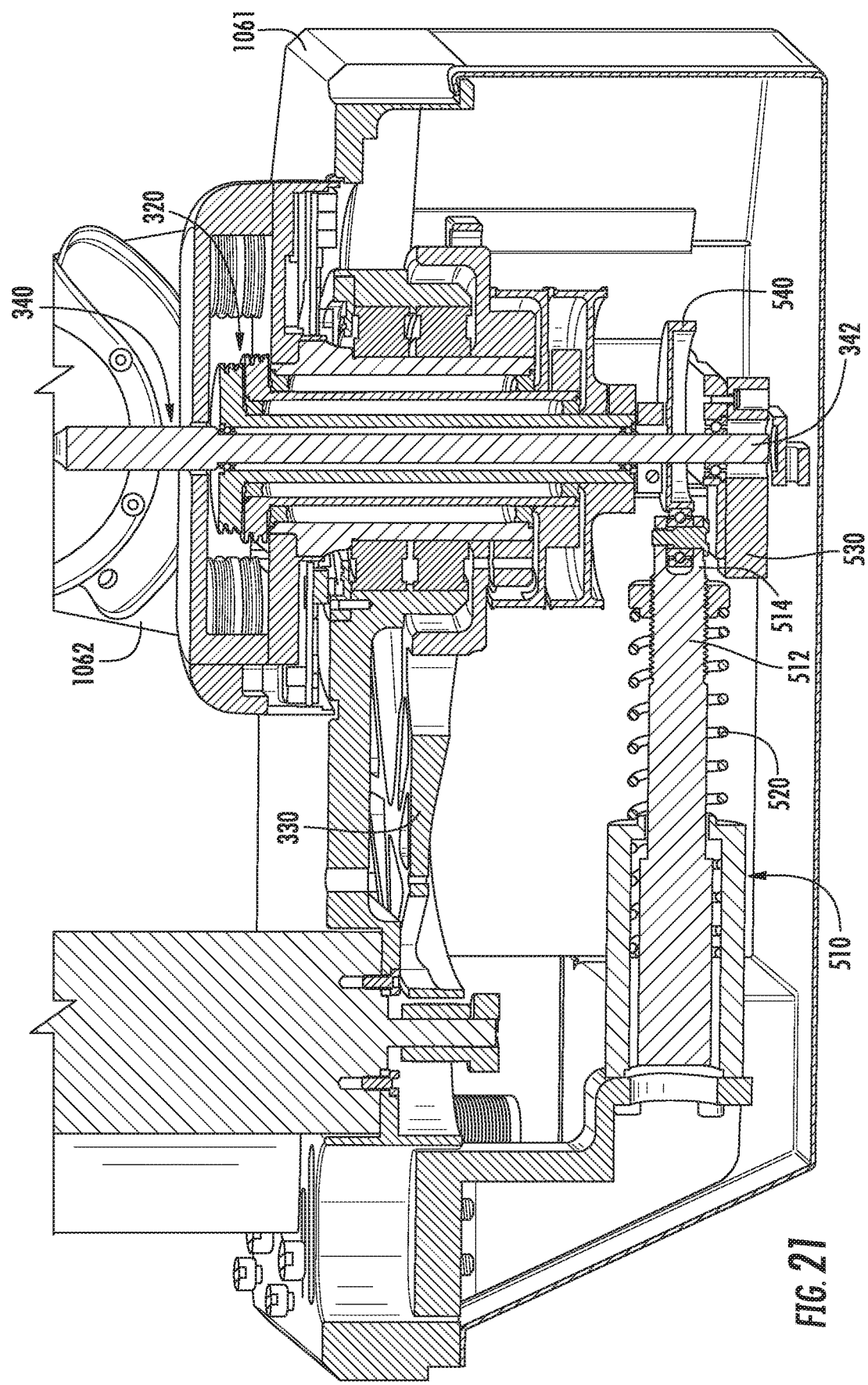
FIG. 21 is a cross-sectional view taken along section line 21-21 of FIG. 19.

The rotational limit extending mechanism 501 includes a plunger 510, a biasing member 520, a cam follower 530, and a cam 540. The cam 540 is disposed about and is rotatably fixed to a lower portion 342 of the connecting shaft 340. The plunger 510 is supported on the base 1061 to support the cam follower 530 in engagement with the cam 540. As shown in FIG. 21, the plunger 510 is positioned orthogonal to the shaft 340; however, it is contemplated that the plunger 510 may be disposed at any angle relative to lower portion 342 of the connecting shaft 340 to maintain the cam follower 530 in engagement with the cam 540.

Figure 24:
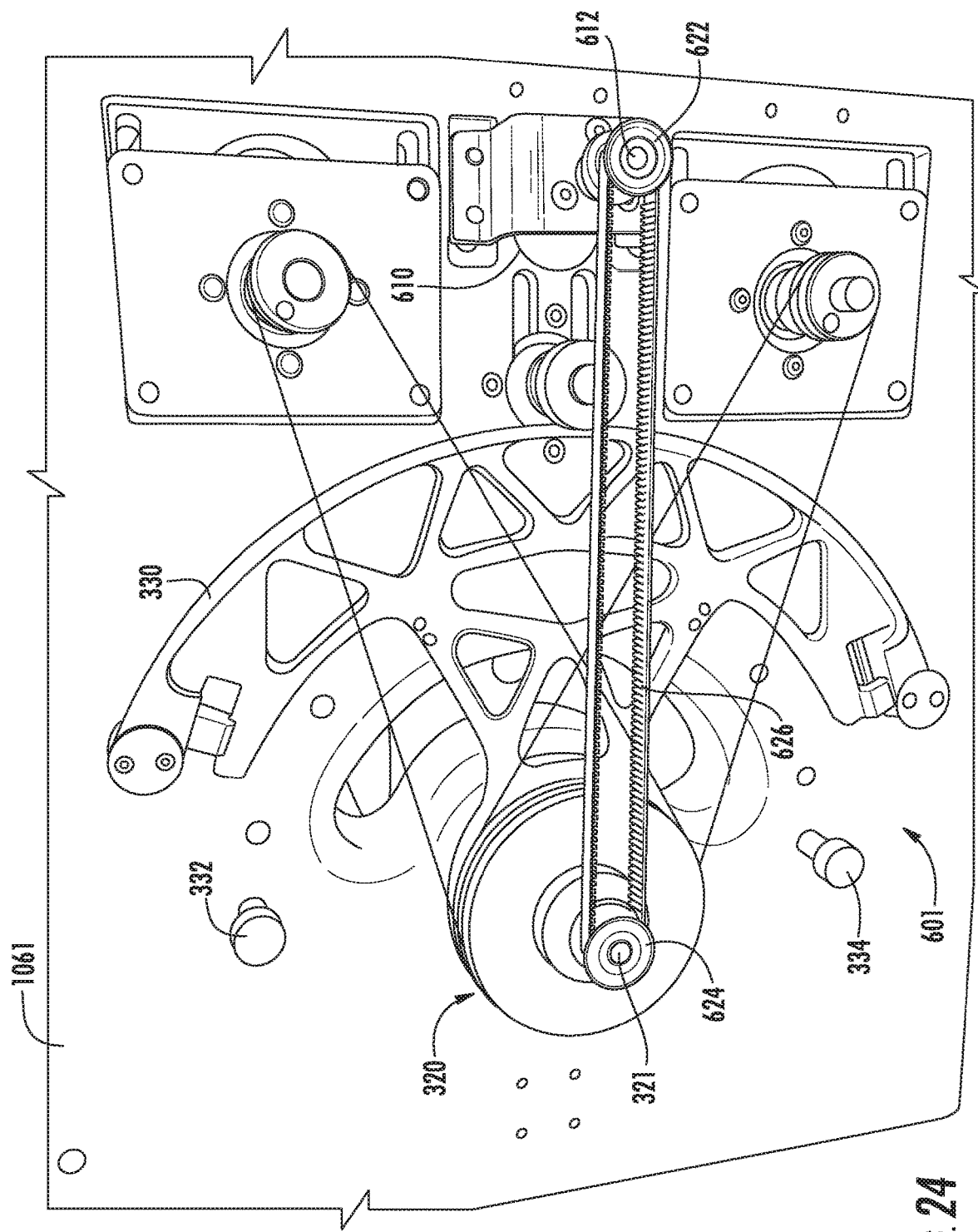
FIG. 24 is a lower perspective view of a control arm including another limit extending mechanism in accordance with the present disclosure.

The swivel member 1062 is rotatably coupled to a flange 330 such that as the swivel member 1062 is rotated relative to the base 1061, the flange 330 rotates about the first axis of rotation $A_1$. The flange 330 is rotatable about the first axis of rotation $A_1$ until the flange 330 engages one of two stops 332, 334 (FIG. 24). When the flange 330 engages one of the stops 332, 334, the flange 330, and thus the swivel member 1062, is prevented from additional rotation relative to the base 1061 in a first direction and is allowed to rotate relative to the base 1061 in a second opposite direction.

Figure 22:
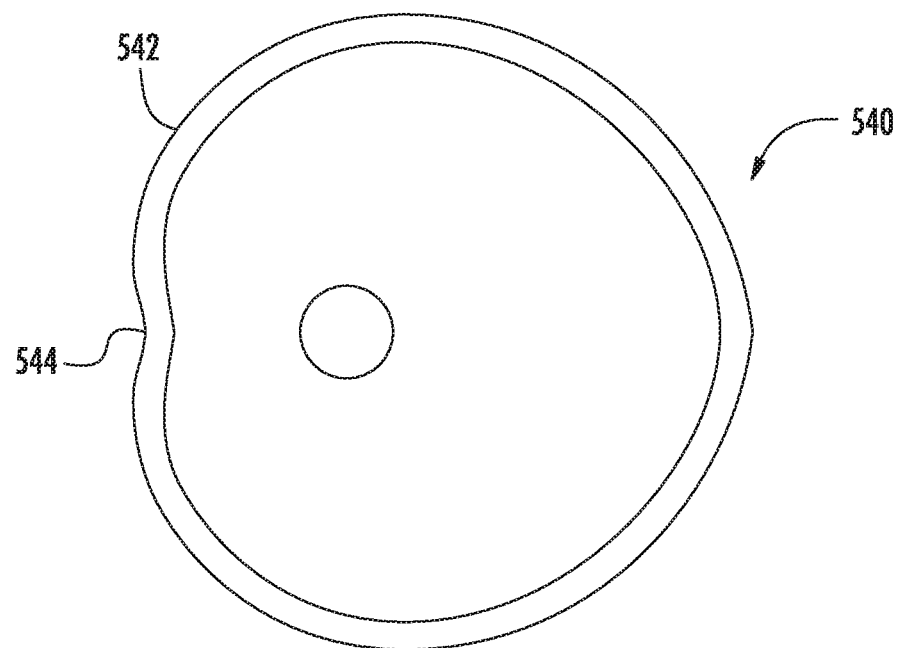
FIG. 22 is a bottom view of a cam of the limit extending mechanism of FIG. 18.

As detailed above with respect to passive axis system 300, the shaft 340 is operably coupled to rotation of the gimbal 70 about a fourth axis of rotation $A_4$. As the swivel member 1062 is rotated relative to the base 1061, the cam follower 530 engages the cam 540 to prevent the shaft 340 from rotating relative to the base 1061. The cam 540 has a camming surface 542 that defines a well 544 as best shown in FIG. 22. The biasing member 520 is disposed about the plunger 510 to urge the cam follower 530 into engagement with the well 544 of the cam 540 to prevent the cam 540, and thus the connecting shaft 340, from rotating relative to the base 1061.

By preventing the connecting shaft 340 from rotating relative to the base 1061, when the gimbal 70 is engaged by a clinician to deliver an input force to the gimbal 70 such that the gimbal 70 is rotated relative to the fourth axis of rotation $A_4$, the swivel member 1062 is rotated about the first axis of rotation $A_1$ by the passive axis system 500. Specifically as detailed above, as the gimbal 70 is rotated about the fourth axis of rotation $A_4$, rotation of the gimbal 370 affects rotation of a gimbal pulley 360. The gimbal pulley 360 is rotatably coupled to an upper pulley 350 by a wire loop 370 such that rotation of the gimbal pulley 360 affects rotation of the upper pulley 350. The upper pulley 350 is rotatably coupled to the upper end 348 of the connecting shaft 340 such that rotation of the upper pulley 350 affects rotation of the connecting shaft 340. As detailed above, the lower portion 342 of the connection shaft 340 is rotatably fixed to the base 1061 by the engagement of the cam follower 530 with the well 544 of the cam 540 such that, in response to the rotation of the lower portion 342 of the connecting shaft 340, the swivel member 1062 is rotated about the first axis of rotation $A_1$ relative to the base 1061. Thus, in response to the input force being applied to the gimbal 70, the swivel member 1062 is rotated about the first axis of rotation $A_1$.

Continuing to refer to FIGS. 18-23, when the flange 330 is engaged with one of the stops 322, the rotational limit extending mechanism 501 also allows the shaft 340 to rotate relative to the base 1061 to permit for the rotation limit of the control arm 1060 to be exceeded. As detailed above, the control arm 60 is rotatable about the first axis of rotation $A_1$ about the base 1061; which a passive axis system (e.g., passive axis system 300 or passive axis system 400) associates with rotation of the gimbal 70 about the fourth axis of rotation $A_4$. The rotation of the control arm 1060 and/or the gimbal 70 about a respective axis may be limited by mechanical stops (e.g., stops 332, 334) to prevent the control arm 60 and/or the gimbal 70 from rotating about a respective axis beyond a threshold limit. As detailed herein below, the rotational limit extending mechanism 501 resists rotation beyond the threshold limit while permitting a clinician to rotate the control arm 1060 and/or gimbal 70 beyond the threshold limit after a predetermined threshold force is exceeded. The rotational limit extending mechanism 501 provides feedback to a clinician when the threshold limit is met and when the threshold limit is exceeded as described in greater detail below.

Referring initially to FIGS. 19 and 20, the cam 540 is coupled and rotatably fixed to a shaft 340. The cam 540 includes a camming surface 542 about the outer surface of the cam 540. The camming surface 542 defines a well 544 as best shown in FIG. 22. The plunger 510 is mounted to the base 1061 substantially orthogonal to the shaft 340 and includes an extendable member 512 having an end 514 that supports the cam follower 530 adjacent the cam 540. The biasing member 520 is positioned about the extendable member 512 of the plunger 510 to urge the end 514 towards the camming surface 542 of the cam 540 such that the cam follower 530 is engaged with the camming surface 542.

Figure 23:
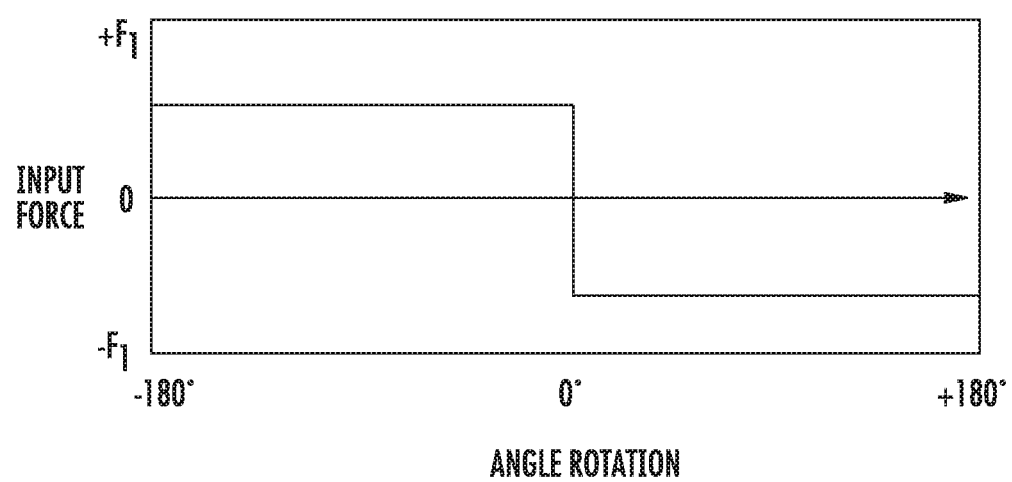
FIG. 23 is a graphical representation of an input force for rotation of the cam in a plurality of angles.

The biasing member 520 is sized to set a threshold limit for rotating the shaft 340 when the swivel member 1062 reaches a rotational limit. With particular reference to FIGS. 22 and 23, the profile of the camming surface 542 is shaped such that a biasing force of the biasing member 520 urges the cam follower 530 towards a centered position where the cam follower 530 engages the well 544 of the cam 540. To rotate the cam 540 from the centered position, an input force is required to overcome the threshold limit exerted on the camming surface 542 of the cam 540 by the cam follower 530 to rotate the cam 540 such that the cam follower 530 is rotated from within the well 544. As shown, the camming surface 542 has a profile such that once an input torque exceeds the force exerted by the biasing member 520 to maintain the cam follower 530 within the well 544 of the cam 540, the input torque required to continue rotation of the cam follower 530 along the camming surface 542 of the cam 540 is equal to the input torque require to initiate rotation of the cam 540 as shown in FIG. 22. Other cam profiles for the camming surface 542 are also contemplated. For example, the cam profile of the camming surface 542 may be asymmetrical about the well 544 or the cam profile of the camming surface 542 may require increasing or decreasing torque to continue rotating the cam 540. It will be appreciated that the cam profile can match or be configured to match any desired torque profile.

The threshold limit of the cam 540 is in a range of about 200 Nmm to about 1200 Nmm (e.g., about 800 Nmm). For example, when the flange 330 reaches a rotational limit in a first direction (e.g., when the flange 330 engages the first stop 332), the rotational limit extending mechanism 501 allows the shaft 340 to rotate relative to the base 1061 in the first direction when an input torque exceeds the threshold limit defined by the engagement of the cam follower 530 with the well 544 of the cam 540. When the input torque exceeds the threshold limit, the rotational limit extending mechanism 501 allows the shaft 340 to rotate relative to the base 1061 until the cam follower 530 is unseated from within the well 544 and travels along the camming surface 542 of the cam 540. When the input torque is reduced below the threshold limit, the biasing force of the biasing member 520 through the engagement of the cam follower 530 with the camming surface 542 rotates the cam 540 towards the centered position to return the cam follower 530 to the well 544.

With reference to FIG. 24, another rotational limit extending mechanism 601 is disclosed in accordance with the present disclosure that resists rotation beyond a threshold limit while permitting a clinician to rotate the control arm 1060 and/or the gimbal 70 beyond the threshold limit after a predetermined threshold torque is exceeded. The rotational limit extending mechanism 601 includes a motor 610 and a connection assembly 620. The motor 610 is mounted to the bottom of the base 61 and includes a drive shaft 612. The drive shaft 612 is rotatably coupled with the shaft 340 by the connection assembly 620. The connection assembly 620 includes a first or motor pulley 622, a second or shaft pulley 624, and a drive member 626. The motor pulley 622 is fixed about the drive shaft 612 and the shaft pulley 624 is fixed to the shaft 340. The drive member 626 is wrapped around the motor pulley 622 to rotatably couple the shaft pulley 624 to the drive shaft 612 of the motor 610 with the shaft 340. As shown, the connection assembly 620 is a pulley/belt mechanism; however, it is contemplated that the connection assembly 620 may also include a gear train that rotatably couples the drive shaft 612 of the motor 610 with the shaft 340.

Similar to the rotational limit extending mechanism 501 detailed above, the rotational limit extending mechanism 601 allows the shaft 340 to rotate relative to the base 1061 when the flange 330 reaches a rotational limit about the shaft 340 when an input force exceeds a threshold limit or torque being applied by the motor 610 to the shaft 340. The threshold torque of the motor 610 is in a range of about 200 Nmm to about 1200 Nmm (e.g., about 800 Nmm). In addition, the threshold torque of the motor 610 may be constant or be varied based on an angular deflection of the shaft 340 (i.e., the rotation of the shaft 340 beyond the rotational limit). Further, the threshold torque of the motor 610 may be determined by an input device engaged with the input shaft 78 of the gimbal 70 and/or by a tool 20 (FIG. 1) attached to a link 12 associated with the control arm 1060.

As detailed above and shown in FIG. 1, the user interface 40 is in operable communication with the robotic system 10 to perform a surgical procedure on a patient "P"; however, it is envisioned that the user interface 40 may be in operable communication with a surgical simulator (not shown) to virtually actuate a robot system and/or tool in a simulated environment. For example, the surgical robot system 1 may have a first mode where the user interface 40 is coupled to actuate the robot system 10 and a second mode where the user interface 40 is coupled to the surgical simulator to virtually actuate a robot system. The surgical simulator may be a standalone unit or be integrated into the processing unit 30. The surgical simulator virtually responds to a clinician interfacing with the user interface 40 by providing visual, audible, force, and/or haptic feedback to a clinician through the user interface 40. For example, as a clinician interfaces with the gimbals 70, the surgical simulator moves representative tools that are virtually acting on tissue at a simulated surgical site. It is envisioned that the surgical simulator may allow a clinician to practice a surgical procedure before performing the surgical procedure on a patient. In addition, the surgical simulator may be used to train a clinician on a surgical procedure. Further, the surgical simulator may simulate "complications" during a proposed surgical procedure to permit a clinician to plan a surgical procedure.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. A control arm for receiving input from a user, the control arm comprising:
    a swivel member rotatable about a first axis;
    a first member having a lower end and an upper end, the lower end of the first member rotatably coupled to the swivel member about a second axis that is orthogonal to the first axis;
    a second member having a first end and a second end, the first end of the second member pivotally coupled, about a third axis, to the upper end of the first member, the third axis parallel to the second axis;
    a gimbal rotatably coupled, about a fourth axis, to the second end of the second member, the fourth axis orthogonal to the third axis; and
    a passive axis system for rotatably associating rotation of the first member about the first axis with rotation of the gimbal about the fourth axis, the passive axis system including a lower disk, a first shaft, an upper disk, a wire loop, and a second shaft, the lower disk rotatably positioned about the first axis adjacent the lower end of the first member, the upper disk positioned adjacent the first end of the second member, the first shaft disposed within the first member to rotatably couple the lower disk to the upper disk, and the wire loop rotatably coupling the upper disk to the second shaft, wherein the passive axis system includes an upper universal joint positioned such that the upper universal joint pivots about the third axis as the second member rotates about the third axis.

2. The control arm according to claim 1, wherein the lower disk is rotatably fixed relative to the swivel member.

3. The control arm according to claim 1, wherein the passive axis system includes a lower universal joint positioned such that the lower universal joint pivots about the second axis as the first member rotates about the second axis.

4. The control arm according to claim 3, wherein the lower universal joint is rotatably coupled to the lower end of the first shaft and is rotatably coupled to the lower disk.

5. The control arm according to claim 1, wherein the upper universal joint is rotatably coupled to the upper end of the first shaft and is rotatably coupled to the upper disk.

6. The control arm according to claim 1, wherein the second shaft rotates the gimbal about the fourth axis in response to rotation of the swivel member about the first axis.

7. The control arm according to claim 6, wherein the second shaft rotates the gimbal in a second direction in response to rotation of the swivel member in a first direction that is opposite to the second direction.

8. The control arm according to claim 7, wherein rotation of the second shaft in the second direction is angularly scaled and opposite to the rotation of the swivel member in the first direction.

9. The control arm according to claim 1, further comprising a fixed mount, the swivel member rotatably coupled about the first axis to the fixed mount.

10. The control arm according to claim 9, wherein the first disk is rotatably fixed relative to the fixed mount.

11. A control arm for receiving input from a user, the control arm comprising:
    a swivel member rotatable about a first axis;
    a first member having a lower end and an upper end, the lower end of the first member rotatably coupled to the swivel member about a second axis that is orthogonal to the first axis;
    a second member having a first end and a second end, the first end of the second member pivotally coupled, about a third axis, to the upper end of the first member, the third axis parallel to the second axis;
    a gimbal rotatably coupled, about a fourth axis, to the second end of the second member, the fourth axis orthogonal to the third axis;
    a passive axis system for rotatably associating rotation of the first member about the first axis with rotation of the gimbal about the fourth axis, the passive axis system including a lower disk, a first shaft, an upper disk, a wire loop, and a second shaft, the lower disk rotatably positioned about the first axis adjacent the lower end of the first member, the upper disk positioned adjacent the first end of the second member, the first shaft disposed within the first member to rotatably couple the lower disk to the upper disk, and the wire loop rotatably coupling the upper disk to the second shaft; and
    a gimbal disk disposed within the second end of the second member and rotatable about the fourth axis, the wire loop passing around the upper disk and the gimbal disk.

12. The control arm according to claim 11, further comprising a gimbal shaft positioned along and rotatable about the fourth axis, the gimbal shaft rotatably coupled to the gimbal disk.

13. The control arm according to claim 12, wherein the gimbal includes:
    a support arm having a first end rotatably fixed to the gimbal shaft;
    a swing arm having a first end rotatably coupled about a fifth axis to a second end of the support arm;
    an input support arm having a first end rotatably coupled about a sixth axis to a second end of the swing arm; and
    an input shaft positioned along a seventh axis and rotatably coupled to a second end of the input support arm.

* * * * *